US012672858B2

(12) United States Patent
Wohl et al.

(10) Patent No.: US 12,672,858 B2
(45) Date of Patent: Jul. 7, 2026

(54) COMPOSITIONS, DEVICES AND METHODS FOR TESTING INANIMATE SURFACES, GROUPS AND INDIVIDUALS FOR PATHOGEN INFECTION

(71) Applicant: 3M Innovative Properties Company, St. Paul, MN (US)

(72) Inventors: Michael Wohl, Bethesda, MD (US); Michael R. Berrigan, Oakdale, MN (US); Narina Y. Stepanova, Woodbury, MN (US); Laura R. Nereng, Woodbury, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 637 days.

(21) Appl. No.: 17/927,345

(22) PCT Filed: May 26, 2021

(86) PCT No.: PCT/US2021/034327
§ 371 (c)(1),
(2) Date: Nov. 22, 2022

(87) PCT Pub. No.: WO2021/242907
PCT Pub. Date: Dec. 2, 2021

(65) Prior Publication Data
US 2023/0200786 A1      Jun. 29, 2023
US 2024/0197294 A2      Jun. 20, 2024

Related U.S. Application Data

(60) Provisional application No. 63/029,974, filed on May 26, 2020.

(51) Int. Cl.
*A61B 10/00* (2006.01)
*G01N 33/497* (2006.01)

(52) U.S. Cl.
CPC ........... *A61B 10/00* (2013.01); *G01N 33/497* (2013.01); *A61B 2010/0087* (2013.01)

(58) Field of Classification Search
CPC .......... A61B 5/082; A61B 5/087; A61B 5/097
(Continued)

(56) References Cited

U.S. PATENT DOCUMENTS 3,998,916 A      12/1976   Turnhout
4,215,682 A      8/1980    Kubik et al.
(Continued)

FOREIGN PATENT DOCUMENTS

CN          203465268 U      3/2014
CN          111296941 A      6/2020
(Continued)

OTHER PUBLICATIONS

PCT International Application No. PCT/US2022/043827, filed Sep. 16, 2022; International Preliminary Report on Patentability issued Mar. 28, 2024, 7 pages.

(Continued)

*Primary Examiner* — Puya Agahi
(74) *Attorney, Agent, or Firm* — Mueting Raasch Group

(57) ABSTRACT

Disclosed herein are compositions, devices and methods for detecting analytes in air samples obtained from a subject. Compositions can be included on inanimate surfaces such as masks to be worn by an individual having a test substrate for capturing analytes.

19 Claims, 17 Drawing Sheets

(58) Field of Classification Search

USPC .......... 600/532; 128/206.12, 206.21, 206.25, 128/206.24; 434/4

See application file for complete search history.

(56) References Cited

U.S. PATENT DOCUMENTS

| RE31,285 | E | 6/1983 | van Turnhout et al. |
|---|---|---|---|
| 4,588,537 | A | 5/1986 | Klaase et al. |
| 4,798,850 | A | 1/1989 | Brown |
| 5,174,959 | A | 12/1992 | Kundu et al. |
| 5,405,584 | A | 4/1995 | Zito |
| 5,496,507 | A | 3/1996 | Angadjivand et al. |
| 5,908,598 | A | 6/1999 | Rousseau et al. |
| 6,085,576 | A | 7/2000 | Sunshine et al. |
| 6,119,691 | A | 9/2000 | Angadjivand et al. |
| 6,375,886 | B1 | 4/2002 | Angadjivand et al. |
| 6,406,657 | B1 | 6/2002 | Eitzman et al. |
| 6,454,986 | B1 | 9/2002 | Eitzman et al. |
| 6,743,464 | B1 | 6/2004 | Insley et al. |
| 6,783,574 | B1 | 8/2004 | Angadjivand et al. |
| 6,814,844 | B2 | 11/2004 | Bhullar et al. |
| 6,824,718 | B2 | 11/2004 | Eitzman et al. |
| 7,947,142 | B2 | 5/2011 | Fox et al. |
| 8,162,153 | B2 | 4/2012 | Fox et al. |
| 9,139,940 | B2 | 9/2015 | Berrigan et al. |
| 9,169,521 | B1 | 10/2015 | Rajagopal et al. |
| 9,284,593 | B2 | 3/2016 | Rajagopal et al. |
| 9,663,819 | B2 | 5/2017 | Jovanovich et al. |
| 9,897,590 | B2 | 2/2018 | Rodriguez et al. |
| 9,907,617 | B2 | 3/2018 | Rogers |
| 10,166,381 | B2 | 1/2019 | Gardner et al. |
| 10,273,612 | B2 | 4/2019 | Song et al. |
| 10,413,216 | B2 | 9/2019 | Hamilton |
| 10,591,460 | B1 | 3/2020 | Ahmad et al. |
| 10,617,780 | B2 | 4/2020 | Dombrowski et al. |
| 11,237,161 | B2 | 2/2022 | Khattak |
| 2001/0036630 | A1 | 11/2001 | Ibrahim |
| 2003/0145858 | A1 | 8/2003 | Cardarelli |
| 2004/0077093 | A1 | 4/2004 | Pan |
| 2004/0226563 | A1 | 11/2004 | Xu et al. |
| 2004/0237674 | A1 | 12/2004 | Wu et al. |
| 2005/0085740 | A1 | 4/2005 | Davis et al. |
| 2005/0180882 | A1 | 8/2005 | Tung et al. |
| 2007/0199567 | A1* | 8/2007 | Kanzer ................ A62B 23/025 |
| | | | 128/206.28 |
| 2008/0075633 | A1 | 3/2008 | Ostrowski et al. |
| 2009/0259146 | A1 | 10/2009 | Freeman et al. |
| 2009/0277451 | A1 | 11/2009 | Weinberg |
| 2010/0087749 | A1 | 4/2010 | Tovey |
| 2011/0098590 | A1 | 4/2011 | Garbutt et al. |
| 2012/0002199 | A1 | 1/2012 | Ben-David et al. |
| 2013/0133663 | A1 | 5/2013 | Maksym et al. |
| 2013/0217029 | A1 | 8/2013 | Sislian et al. |
| 2014/0065689 | A1 | 3/2014 | Hogan et al. |
| 2014/0097116 | A1 | 4/2014 | Hollander |
| 2014/0180156 | A1 | 6/2014 | Ku et al. |
| 2014/0234873 | A1 | 8/2014 | Leck et al. |
| 2014/0246334 | A1 | 9/2014 | Bosch et al. |
| 2014/0334980 | A1 | 11/2014 | Graham et al. |
| 2014/0366609 | A1 | 12/2014 | Beck et al. |
| 2015/0024379 | A1 | 1/2015 | Ensor et al. |
| 2015/0033824 | A1 | 2/2015 | Hammarlund et al. |
| 2015/0118683 | A1 | 4/2015 | Li et al. |
| 2015/0226585 | A1 | 8/2015 | Yang |
| 2015/0299761 | A1 | 10/2015 | Hattan |
| 2015/0377748 | A1 | 12/2015 | Cooper et al. |
| 2016/0015098 | A1 | 1/2016 | Conlon |
| 2016/0022946 | A1 | 1/2016 | Sislian et al. |
| 2016/0202222 | A1 | 7/2016 | Roberts et al. |
| 2016/0274100 | A1 | 9/2016 | Kobayashi |
| 2016/0363555 | A1 | 12/2016 | Kang et al. |
| 2017/0036205 | A1 | 2/2017 | Bishop et al. |
| 2017/0067803 | A1 | 3/2017 | Jackson et al. |
| 2017/0122931 | A1 | 5/2017 | Carnahan et al. |
| 2017/0153238 | A1 | 6/2017 | Birse et al. |

| 2018/0242884 | A1 | 8/2018 | Kulkarni et al. |
|---|---|---|---|
| 2018/0263531 | A1 | 9/2018 | Stambeck |
| 2018/0369618 | A1 | 12/2018 | Wang |
| 2019/0231222 | A1 | 8/2019 | Ahmad et al. |
| 2020/0110092 | A1 | 4/2020 | Ahmad et al. |
| 2020/0245898 | A1 | 8/2020 | Heanue et al. |
| 2020/0282171 | A1* | 9/2020 | Al-Jumaily ............... C08F 2/38 |
| 2020/0397340 | A1 | 12/2020 | Dweik |
| 2021/0059560 | A1 | 3/2021 | Allegra et al. |
| 2021/0129136 | A1 | 5/2021 | Neuman et al. |
| 2021/0140957 | A1 | 5/2021 | Chou et al. |
| 2021/0177382 | A1 | 6/2021 | Perdue et al. |
| 2021/0370001 | A1* | 12/2021 | Wakabayashi .... A61M 16/0003 |
| 2022/0023867 | A1 | 1/2022 | Kedia et al. |
| 2022/0125333 | A1 | 4/2022 | Alburty et al. |
| 2022/0195539 | A1 | 6/2022 | Hogan et al. |
| 2022/0236147 | A1 | 7/2022 | Call et al. |
| 2023/0200786 | A1 | 6/2023 | Wohl |
| 2023/0242968 | A1 | 8/2023 | Wohl |
| 2024/0068054 | A1 | 2/2024 | Wohl |
| 2024/0091769 | A1 | 3/2024 | Wohl |

FOREIGN PATENT DOCUMENTS

| EP | 2 098 166 A1 | 9/2009 |
|---|---|---|
| EP | 3 351 171 A1 | 7/2018 |
| EP | 2023/002406 A1 | 1/2023 |
| EP | 2023/002410 A1 | 1/2023 |
| JP | 2010-516298 A | 5/2010 |
| JP | 2013-063266 A | 4/2013 |
| KR | 102026892 B2 | 11/2019 |
| WO | WO 2008/097307 A2 | 8/2008 |
| WO | WO 2011/106384 A1 | 9/2011 |
| WO | WO 2012/068374 A2 | 5/2012 |
| WO | WO 2013/132085 A1 | 9/2013 |
| WO | WO 2015/166246 A1 | 11/2015 |
| WO | WO 2019/084092 A1 | 5/2019 |
| WO | WO 2019/178247 A1 | 9/2019 |
| WO | WO 2020/023906 A2 | 1/2020 |
| WO | WO 2019-150955 A1 | 8/2020 |
| WO | WO 2020/170169 A2 | 8/2020 |
| WO | WO 2020/243369 A1 | 12/2020 |
| WO | WO 2021/046278 A1 | 3/2021 |
| WO | WO 2021/216386 A1 | 10/2021 |
| WO | WO 2021/246566 A1 | 12/2021 |
| WO | WO 2022/015765 A2 | 1/2022 |
| WO | WO 2022/031570 A1 | 2/2022 |
| WO | WO 2022/093876 A1 | 5/2022 |
| WO | WO 2022/155392 A1 | 7/2022 |
| WO | WO 2021/242907 A1 | 8/2022 |
| WO | WO 2022/165230 A1 | 8/2022 |
| WO | WO 2022/172222 A1 | 8/2022 |
| WO | WO 2022/192295 A1 | 9/2022 |
| WO | WO 2022/208359 A1 | 10/2022 |
| WO | WO 2022/214884 A1 | 10/2022 |
| WO | WO 2022/234044 A1 | 11/2022 |
| WO | WO 2022/243753 A1 | 11/2022 |
| WO | WO 2022/243902 A1 | 11/2022 |
| WO | WO 2022/248992 A1 | 12/2022 |
| WO | WO 2022/249061 A1 | 12/2022 |
| WO | WO 2023/002406 A1 | 1/2023 |
| WO | WO 2023/002410 A1 | 1/2023 |
| WO | WO 2023/044021 A1 | 3/2023 |
| WO | WO 2023/073503 A1 | 5/2023 |

OTHER PUBLICATIONS

U.S. Appl. No. 63/029,974, filed May 26, 2020, Wohl.
U.S. Appl. No. 63/051,116, filed Jul. 13, 2020, Wohl.
U.S. Appl. No. 63/136,723, filed Jan. 13, 2021, Wohl.
U.S. Appl. No. 63/142,874, filed Jan. 28, 2021, Wohl.
U.S. Appl. No. 63/148,195, filed Feb. 11, 2021, Wohl.
U.S. Appl. No. 63/158,153, filed Mar. 8, 2021, Wohl.
U.S. Appl. No. 63/200,058, filed Feb. 12, 2021, Berrigan et al.
U.S. Appl. No. 63/200,901, filed Apr. 2, 2021, Sherman et al.
U.S. Appl. No. 63/200,958, filed Apr. 6, 2021, Sherman et al.
U.S. Appl. No. 63/201,981, filed May 21, 2021, Berrigan et al.

(56) References Cited

OTHER PUBLICATIONS

U.S. Appl. No. 63/201,983, filed May 21, 2021, Berrigan et al.
U.S. Appl. No. 63/202,140, filed May 28, 2021, Berrigan et al.
U.S. Appl. No. 63/202,143, filed May 28, 2021, Berrigan et al.
U.S. Appl. No. 63/203,441, filed Jul. 22, 2021, Sherman et al.
U.S. Appl. No. 63/203,442, filed Jul. 22, 2021, Sherman et al.
U.S. Appl. No. 63/203,831, filed Aug. 2, 2021, Sherman et al.
U.S. Appl. No. 63/222,745, filed Jul. 16, 2021, Wohl.
U.S. Appl. No. 63/224,242, filed Jul. 21, 2021, Wohl.
U.S. Appl. No. 63/227,498, filed Jul. 30, 2021, Berrigan et al.
U.S. Appl. No. 63/227,519, filed Jul. 30, 2021, Sherman et al.
U.S. Appl. No. 63/227,529, filed Jul. 30, 2021, Berrigan et al.
U.S. Appl. No. 63/227,534, filed Jul. 30, 2021, Berrigan et al.
U.S. Appl. No. 63/227,608, filed Jul. 30, 2021, Berrigan et al.
U.S. Appl. No. 63/237,909, filed Aug. 27, 2021, Wohl.
U.S. Appl. No. 63/245,021, filed Sep. 16, 2021, Wohl.
U.S. Appl. No. 63/255,363, filed Oct. 13, 2021, Wohl.
U.S. Appl. No. 63/260,828, filed Sep. 1, 2021, Berrigan et al.
U.S. Appl. No. 63/273,300, filed Oct. 29, 2021, Sherman et al.
U.S. Appl. No. 63/283,075, filed Nov. 24, 2021, Wohl.
U.S. Appl. No. 63/287,911, filed Dec. 9, 2021, Wohl.
U.S. Appl. No. 63/306,273, filed Feb. 3, 2022, Sherman et al.
"3M™ Curos™ Disinfecting Port Protectors" Web page from 3M, believed to be available at least as early as Jan. 30, 2024 [online]. Retrieved from the Internet: <URL:https://www.3m.com/3M/en_US/medical-us/disinfecting-port-protectors/>, 12 pages, [retrieved on Jan. 30, 2023].
"Black people dying from coronavirus at much higher rates in cities across the USA," Web page from USA Today, Updated Apr. 9, 2020 [online]. Retrieved from the Internet: <URL:https://www.usatoday.com/story/news/nation/2020/04/07/who-dying-coronavirus-more-black-people-die-major-cities/2961323001/>, 6 pages, [retrieved on Nov. 29, 2023].
"Cellex qSARS-CoV-2 IgG/IgM Rapid Test," Package Insert, Catalog No. 5515C025, 5515C050, 5515C100, Cellex Inc., believed to be available at least as early as Jun. 12, 2020, 5 pages.
"Coronavirus (COVID-19) Update: FDA Authorizes First COVID-19 Test for Self-Testing at Home," Web page from fda.gov, Nov. 17, 2020 [online]. Retrieved from the Internet: <URL:https://www.fda.gov/news-events/press-announcements/coronavirus-covid-19-update-fda-authorizes-first-covid-19-test-self-testing-home#:~:text=FDA%20News%20Release-,Coronavirus%20(COVID%2D19)%20Update%3A%20FDA%20Authorizes%20First%20COVID,for%20Self%2DTesting%20at%20Home&text=Today%2C%20the%20U.S.%20Food%20and,and%20that%20provides%20rapid%20results.>, 3 pages, [retrieved on Sep. 11, 2021].
"DPP® COVID-19 IgM/IgG System," Package Insert, Chembio Diagnostic Systems, Inc., Apr. 2, 2020, 31 pages.
"Editorial: COVID-19 is disproportionately killing minorities. That's not a coincidence," Web page from The LA Times, Apr. 8, 2020 [online]. Retrieved from the Internet: <URL:https://www.latimes.com/opinion/story/2020-04-08/coronavirus-racial-disparity>, 4 pages, [retrieved on Nov. 29, 2023].
"FDA authorizes Ellume COVID-19 Home Test as First Over-the-Counter Fully At-Home Diagnostic Test," Web page from ellumehealth.com, Dec. 15, 2020 [online]. Retrieved from the Internet: <URL:https://www.ellumehealth.com/news/fda-authorizes-ellume-covid-19-home-test-as-first-over-the-counter-fully-at-home-diagnostic-test-december-15-2020>, 7 pages, [retrieved on Sep. 11, 2021].
"Instructions for Use—VITROS Immunodiagnostic Products Anti-SARS-CoV-2 Total Reagent Pack—VITROS Immunodiagnostic Products Anti-SARS-CoV-2 Total Calibrator," Package Insert, Ortho Clinical Diagnostics, Version 3.3, Mar. 17, 2021, 23 pages.
"Mayo Clinic named national site for Convalescent Plasma Expanded Access Program," Web page from mayoclinic.org, Apr. 3, 2020 [online]. Retrieved from the Internet: <URL:https://newsnetwork.mayoclinic.org/discussion/mayo-clinic-named-national-site-for-convalescent-plasma-expanded-access-program/>, 5 pages, [retrieved on Nov. 29, 2023].

"Nearly 17 million have lost their jobs, overwhelming state unemployment agencies," Web page from People's World, Apr. 9, 2020 [online]. Retrieved from the Internet: <URL:https://www.peoplesworld.org/article/nearly-17-million-have-lost-their-jobs-overwhelming-state-unemployment-agencies/>, 7 pages, [retrieved on Nov. 29, 2023].
"New At-Home COVID Test: Results in Minutes—First at-home, virtually guided service brings our BinaxNOW COVID-19 test into the home," Web page from abbott.com, Dec. 16, 2020 [online]. Retrieved from the Internet: <URL:https://www.abbott.com/corpnewsroom/diagnostics-testing/new-at-home-covid-test.html#:~:text=The%20BinaxNOW%20test%2C%20which%20provides,people%20through%20the%20testing%20process.>, 4 pages, [retrieved on Sep. 11, 2021].
"WarmStart Colorimetric LAMP 2X Master Mix (DNA & RNA)," Web page from neb.com, believed to be available at least as early as Jan. 16, 2023 [online]. Retrieved from the Internet: <URL:https://www.neb.com/en-us/products/m1800-warmstart-colorimetric-lamp-2x-master-mix-dna-rna#Product%20Information>, 3 pages, [retrieved on Jan. 16, 2023].
"WarmStart Colorimetric LAMP 2X Master Mix Typical LAMP Protocol (M1800)," Web page from www.neb.com, believed to be available at least as early as Jan. 16, 2023 [online]. Retrieved from the Internet: <URL:https://www.neb.com/en-us/protocols/2016/08/15/warmstart-colorimetric-lamp-2x-master-mix-typical-lamp-protocol-m1800>, 2 pages, [retrieved on Jan. 16, 2023].
Bui et al., "Bioaerosol sampling to detect avian influenza virus in Hanoi's largest live poultry market," Mar. 2019, Clinical Infectious Diseases, 68(6):972-975.
Cazacu et al., "Comparison of a New Lateral-Flow Chromatographic Membrane Immunoassay to Viral Culture for Rapid Detection and Differentiation of Influenza A and B Viruses in Respiratory Specimens," Aug. 2004, Journal of Clinical Microbiology, 42(8):3661-3664.
Curtis et al., "Isothermal amplification using a chemical heating device for point-of-care detection of HIV-1," Feb. 2012, PloS ONE, 7(2):e31432.
Ganguli et al., "Rapid isothermal amplification and portable detection system for SARS-CoV-2.," Sep. 2020, Proceedings of the National Academy of Science, 117(37):22727-22735.
Ghosh et al., "Development of a recombinase polymerase based isothermal amplification combined with lateral flow assay (HLB-RPA-LFA) for rapid detection of 'Candidatus Liberibacter asiaticus'," Dec. 2018, PloS ONE, 13(12):e0208530.
He et al., "Temporal dynamics in viral shedding and transmissibility of COVID-19," May 2020, Nature Medicine, 26(5):672-675.
Jamal et al., "Sensitivity of nasopharyngeal swabs and saliva for the detection of severe acute respiratory syndrome coronavirus 2," Mar. 2021, Clinical Infectious Diseases. 72(6):1064-1066.
Jarvis et al., "Temporal dynamics of viral load and false negative rate influence the levels of testing necessary to combat COVID-19 spread," Apr. 2021, Scientific Reports, 11(1):9221.
Kucirka et al., "Variation in false-negative rate of reverse transcriptase polymerase chain reaction-based SARS-CoV-2 tests by time since exposure," Aug. 2020, Annals of Internal Medicine, 173(4):262-267.
Leung et al., "Respiratory virus shedding in exhaled breath and efficacy of face masks," May 2020, Nature Medicine, 26(5):676-680.
PCT International Application No. PCT/IB2022/051250, filed Feb. 11, 2022; International Preliminary Report on Patentability issued Aug. 24, 2023; 10 pages.
PCT International Application No. PCT/IB2022/051250, filed Feb. 11, 2022; International Search Report and Written Opinion issued May 2, 2022; 14 pages.
PCT International Application No. PCT/IB2022/051251, filed Feb. 11, 2022; International Preliminary Report on Patentability issued Nov. 30, 2023; 13 pages.
PCT International Application No. PCT/IB2022/051251, filed Feb. 11, 2022; International Search Report and Written Opinion issued Jun. 23, 2022; 18 pages.

(56)        References Cited

OTHER PUBLICATIONS

PCT International Application No. PCT/IB2022/051252, filed Feb. 11, 2022; International Preliminary Report on Patentability issued Oct. 19, 2023; 14 pages.

PCT International Application No. PCT/IB2022/051252, filed Feb. 11, 2022; International Search Report and Written Opinion issued Jun. 23, 2022; 19 pages.

PCT International Application No. PCT/IB2022/052903, filed Mar. 29, 2022; International Preliminary Report on Patentability issued Oct. 12, 2023; 10 pages.

PCT International Application No. PCT/IB2022/052903, filed Mar. 29, 2022; International Search Report and Written Opinion issued Jun. 8, 2022; 13 pages.

PCT International Application No. PCT/IB2022/054633, filed May 18, 2022; International Preliminary Report on Patentability issued Nov. 30, 2023; 11 pages.

PCT International Application No. PCT/IB2022/054633, filed May 18, 2022; International Search Report and Written Opinion issued Jul. 29, 2022; 15 pages.

PCT International Application No. PCT/IB2022/054683, filed May 19, 2022; International Preliminary Report on Patentability issued Dec. 7, 2023; 8 pages.

PCT International Application No. PCT/IB2022/054683, filed May 19, 2022; International Search Report and Written Opinion issued Aug. 31, 2022; 10 pages.

PCT International Application No. PCT/IB2022/054852, filed May 24, 2022; International Preliminary Report on Patentability issued Dec. 7, 2023; 8 pages.

PCT International Application No. PCT/IB2022/054852, filed May 24, 2022; International Search Report and Written Opinion issued Aug. 19, 2022; 11 pages.

PCT International Application No. PCT/IB2022/056708, filed Jul. 20, 2022; International Preliminary Report on Patentability issued Feb. 1, 2024; 8 pages.

PCT International Application No. PCT/IB2022/056708, filed Jul. 20, 2022; International Search Report and Written Opinion issued Oct. 20, 2022; 11 pages.

PCT International Application No. PCT/IB2022/056714, filed Feb. 11, 2022; International Preliminary Report on Patentability issued Feb. 1, 2024; 8 pages.

PCT International Application No. PCT/IB2022/056714, filed Jul. 20, 2022; International Search Report and Written Opinion issued Nov. 7, 2022; 12 pages.

PCT International Application No. PCT/IB2022/059989, filed Oct. 18, 2022; International Search Report and Written Opinion issued Jan. 17, 2023; 12 pages.

PCT International Application No. PCT/US2021/034327, filed May 26, 2021; International Search Report and Written Opinion issued Aug. 30, 2021; 15 pages.

PCT International Application No. PCT/US2021/034327, filed May 26, 2021; International Preliminary Report on Patentability issued Dec. 8, 2022; 10 pages.

PCT International Application No. PCT/US2021/041485, filed Jul. 13, 2021; International Search Report and Written Opinion issued Dec. 29, 2021; 13 pages.

PCT International Application No. PCT/US2021/041485, filed Jul. 13, 2021; International Preliminary Report on Patentability issued Jan. 26, 2023; 10 pages.

PCT International Application No. PCT/US2022/012392, filed Jan. 14, 2022; International Preliminary Report on Patentability issued Aug. 31, 2023; 96 pages.

PCT International Application No. PCT/US2022/012392, filed Jan. 14, 2022; International Search Report and Written Opinion issued Jun. 8, 2022; 13 pages.

PCT International Application No. PCT/US2022/014388, filed Jan. 28, 2022; International Search Report and Written Opinion issued May 5, 2022; 8 pages.

PCT International Application No. PCT/US2022/014388, filed Jan. 28, 2022; International Preliminary Report on Patentability issued Aug. 3, 2023; 19 pages.

PCT International Application No. PCT/US2022/019399, filed Mar. 8, 2022; International Search Report and Written Opinion issued May 23, 2022; 11 pages.

PCT International Application No. PCT/US2022/043827, filed Sep. 16, 2022; International Search Report and Written Opinion issued Jan. 17, 2023; 9 pages.

Phuphuakrat et al., "Detectable duration of viable SARS-CoV-2, total and subgenomic SARS-CoV-2 RNA in noncritically ill COVID-19 patients: a prospective cohort study," Jun. 2022, Microbiology Spectrum, 10(3):e00503-e00522.

Streeck et al., "Preliminary results and conclusions of the COVID-19 case cluster study (Municipality of Gangelt)," Apr. 2020, Bonn University Hospital, 4 pages (with Machine Translation).

Torretta et al., "Diagnosis of SARS-CoV-2 by RT-PCR using different sample sources: review of the literature," Apr. 2021, Ear, Nose & Throat Journal, 100(2_suppl):131S-138S.

Turgeon et al., "Comparison of five bacteriophages as models for viral aerosol studies," Jul. 2014, Applied and Environmental Microbiology, 80(14):4242-4250.

"3M™ Curos™ Disinfecting Port Protectors" Web page from 3M, product believed to be available at least as early as Feb. 2017. Retrieved from the Internet: <URL:https://www.3m.com/3M/en_US/medical-us/disinfecting-port-protectors/>, 12 pages, [retrieved on Jan. 30, 2023].

EP Patent Application No. 21812036.8, filed Dec. 22, 2022, Extended European Search Report issued May 17, 2024, 8 pages.

EP Patent Application No. 21841893.7, filed Dec. 22, 2022; Extended European Search Report issued Nov. 5, 2024; 9 pages.

CN Patent Application No. 202180059960.3, filed Jan. 19, 2023; 2nd Office Action issued Feb. 2, 2026.

IN Patent Application No. 202247073833, filed Dec. 20, 2022; First Examination Report issued Feb. 13, 2026.

* cited by examiner

COMPOSITIONS, DEVICES AND METHODS FOR TESTING INANIMATE SURFACES, GROUPS AND INDIVIDUALS FOR PATHOGEN INFECTION

CROSS-REFERENCE TO RELATED APPLICATIONS

This application is the § 371 U.S. National Stage of International Application No. PCT/US2021/034327, filed May 26, 2021, which claims priority to and the benefit of U.S. Provisional Patent Application Ser. No. 63/029,974, filed on May 26, 2020, which are hereby incorporated by reference in their entireties.

BACKGROUND OF THE DISCLOSURE

The present disclosure generally relates to medicine, as well as overall industrial and environmental hygiene. More particularly, the present disclosure is directed to compositions, devices and methods for analytes in air samples obtained from individuals.

Medical monitoring and diagnosis involve sample collection and analysis. Sample collection can involve invasive methods and non-invasive methods. Invasive methods of sample collection include procedures such as surgery and blood draws that can cause pain, discomfort, and stress to the patient. Milder forms of invasive methods of sample collection can include swabbing. Devices used in invasive sample collection methods can also be expensive and require aseptic handling to prevent contamination of the sample. Non-invasive methods of collecting samples can be advantageous over invasive sample collection methods by reducing pain and discomfort in the individual during sample collection.

The rapid detection and identification of pathogens is important for the prevention and monitoring for the presence and spread of infection, including preventing and mitigating the spread of global pandemics. Surfaces and individuals are administered tests to detect the presence of pathogens such that appropriate diagnosis, further testing and/or treatment of an individual can be administered. Individuals can also be administered tests to detect circulating antibodies to pathogens, which indicates that the individual had been exposed to the pathogen in the past and generated an immune response to combat infection.

Detection and identification of analytes such as biomarkers can aid in the diagnosis and/or progression of disease, determine effectiveness and/or response to treatment, and allow for correcting and/or adjusting dosage of therapy. Detection of analytes can also be used to detect environmental exposure to potentially harmful chemicals and drug use such as illicit drug use. Detection of biomarkers can also provide information relating to internal physiological states, including disease, metabolic conditions, toxins and the presence of certain chemicals.

Current testing cannot deliver societal needs during pandemics such as the COVID-19 pandemic. For example, during the COVID-19 pandemic there was a time where approximately 500,000 tests were performed daily when more than 20 million daily tests were needed, demonstrating a testing scale gap. Current testing also suffers from drawbacks and challenges such as scaling, sample collection and extraction, testing costs, pain associated with sample collection, risk of transmission, ineffectiveness of testing (e.g., temperature checks), and failure to test asymptomatic people. Current testing also misses the fundamental metric of who is transmitting the disease.

Current testing using a nasal swab for sample collection suffers from a limited supply of swabs, sample collection can be painful and uncomfortable, and requires collection by a trained healthcare professional. Collection of samples such as saliva, sputum, drool, lavage and other oral fluid samples can require specialized equipment and further processing to separate analytes from the oral fluids. No matter what method of sample collection is used, the sample obtained can begin to degrade and sample collection reagents can suffer from supply-chain delays. The sample must then be removed or separated from the collection device, which can be inefficient and affect sensitivity of the test used to analyze the sample. Collection devices for collecting saliva and nasal samples add complexity and suffer from contamination of the underlying sample collection matrix—i.e. saliva and nasal swabs contain many chemicals that need to be removed before extracting the target analyte. Proteases and RNAses can also degrade the target analyte after extraction. The ratio of surface area of the collection material to necessary elution and extraction buffer affects the concentration of target analyte. The greater the concentration of target analyte, the more sensitive the test. Identifying optimal materials to form factors and performance provides the maximum test sensitivity.

Accordingly, there exists a need to develop compositions, devices including the compositions, and methods for using the compositions for testing surfaces, groups and individuals for analytes. Testing exhaled bio-aerosols inexpensively across the globe is a critical unmet need in the market.

BRIEF DESCRIPTION

In one aspect, the present disclosure is directed to a mask insert that comprises a first layer, a test substrate for capturing an analyte in an air sample obtained from a subject, and a second layer, wherein the first layer and the second layer form an outer layer substantially surrounding the test substrate, wherein overlapping regions of the first layer and the second layer are bonded, wherein at least a portion of the test substrate is bonded to at least one of the first layer and the second layer, and wherein the test substrate is configured to be separated from at least a portion of the outer layer.

In one aspect, the present disclosure is directed to a system that comprises a mask insert, the mask insert comprising a first layer, a test substrate for capturing an analyte in an air sample obtained from a subject, and a second layer, wherein the first layer and the second layer form an outer layer substantially surrounding the test substrate, wherein overlapping regions of the first layer and the second layer are bonded, wherein at least a portion of the test substrate is bonded to at least one of the first layer and the second layer, and wherein the test substrate is configured to be separated from at least a portion of the outer layer; and a mask worn by a user, wherein the mask insert is coupled to a surface of the mask.

In another aspect, the present disclosure is directed to a method for detecting the presence of an analyte in an air sample obtained from a subject, the method comprising: collecting from the individual a test substrate worn by the subject; and analyzing the test substrate for the analyte.

DESCRIPTION OF THE DRAWINGS

The disclosure will be better understood and features, aspects and advantages other than those set forth above will become apparent when consideration is given to the following detailed description thereof. Such detailed description makes reference to the following drawings, wherein:

FIG. 2 is an illustration depicting a front view of an embodiment of a mask insert showing the separation of a portion of the outer layer to reveal the test substrate. The patient or healthcare provider pinches the outer layers at each end of the mask insert and pulls outwards in the direction of the large arrows (pulling force indicated by large arrows). The pinch points for the device can be asymmetric. The pinch point on the right of the illustration pinches the outer layer and inner test substrate. The pinch point on the left of the illustration only pinches the outer layers. By pinching the ends and pulling outwards, the perforations allow the removal of the outer protective layers on the left side while maintaining a protective layer to hold the inner test substrate on the right side. After removing a portion of the outer layer, the patient or healthcare provider holds outer protective layers at the pinch point on the right of the illustration to protect the test substrate from being touched by hands that may contain RNAses, proteases and other contaminates. Patient or health care provider can then place collection substrate in a vial for testing.

FIG. 13A depicts an exemplary embodiment of a test substrate having 4 tab portions and a label portion. The test substrate can have perforations parallel to the top edge (and below the label portion) and between individual tabs such that tabs can be independently removed from the test substrate. FIG. 13B depicts an exemplary embodiment of a test substrate having 4 tab portions and a label portion. The tab portions are separated by a gap, but are attached to the label portion. The test substrate can have perforations parallel to the top edge (and below the label portion) and between individual tabs such that tabs can be independently removed from the test substrate. FIG. 13C depicts an exemplary embodiment of a test substrate having four unconnected tab portions.

FIG. 15 shows an inner collection substrate of corrugated, double-sided polyester swab material, protected on all sides from touch, and having very high surface area. The inner tab releases when perforation is cut or torn off Individual tabs are consistently sized for quantification purposes. Tabbed anti-microbial front and back outer layers 120 allow for airflow and protect the inner layer 110 from RNase and other contaminants.

DESCRIPTION

The present disclosure is generally related to compositions, devices and methods for testing inanimate surfaces, groups and individuals for pathogen infection. In particular, the present disclosure is directed to devices for detecting analytes in air samples expired by a subject.

Figure 1:
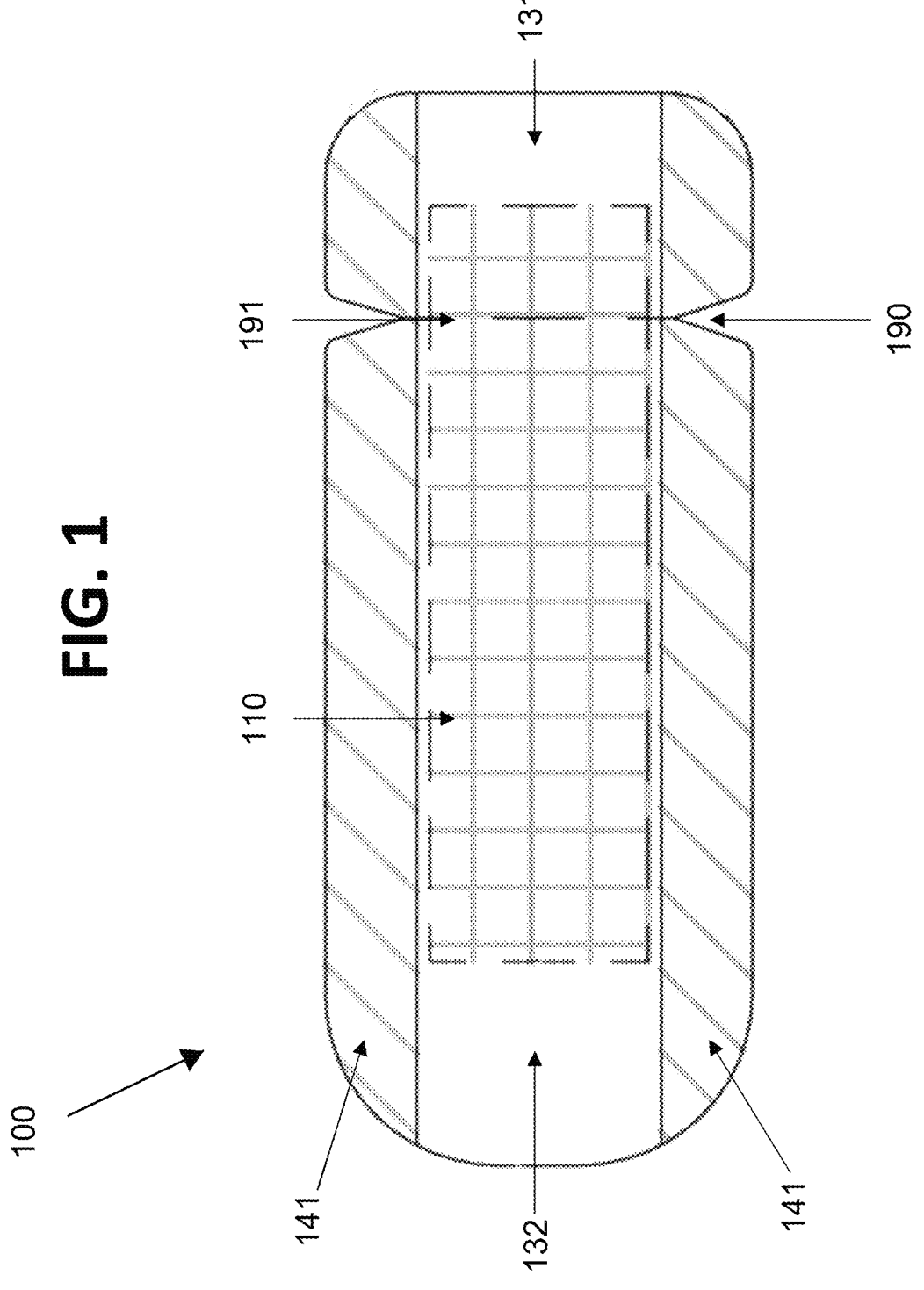
FIG. 1 is an illustration depicting a front view of an embodiment of a mask insert.
Figures 2, 2A, 2B:
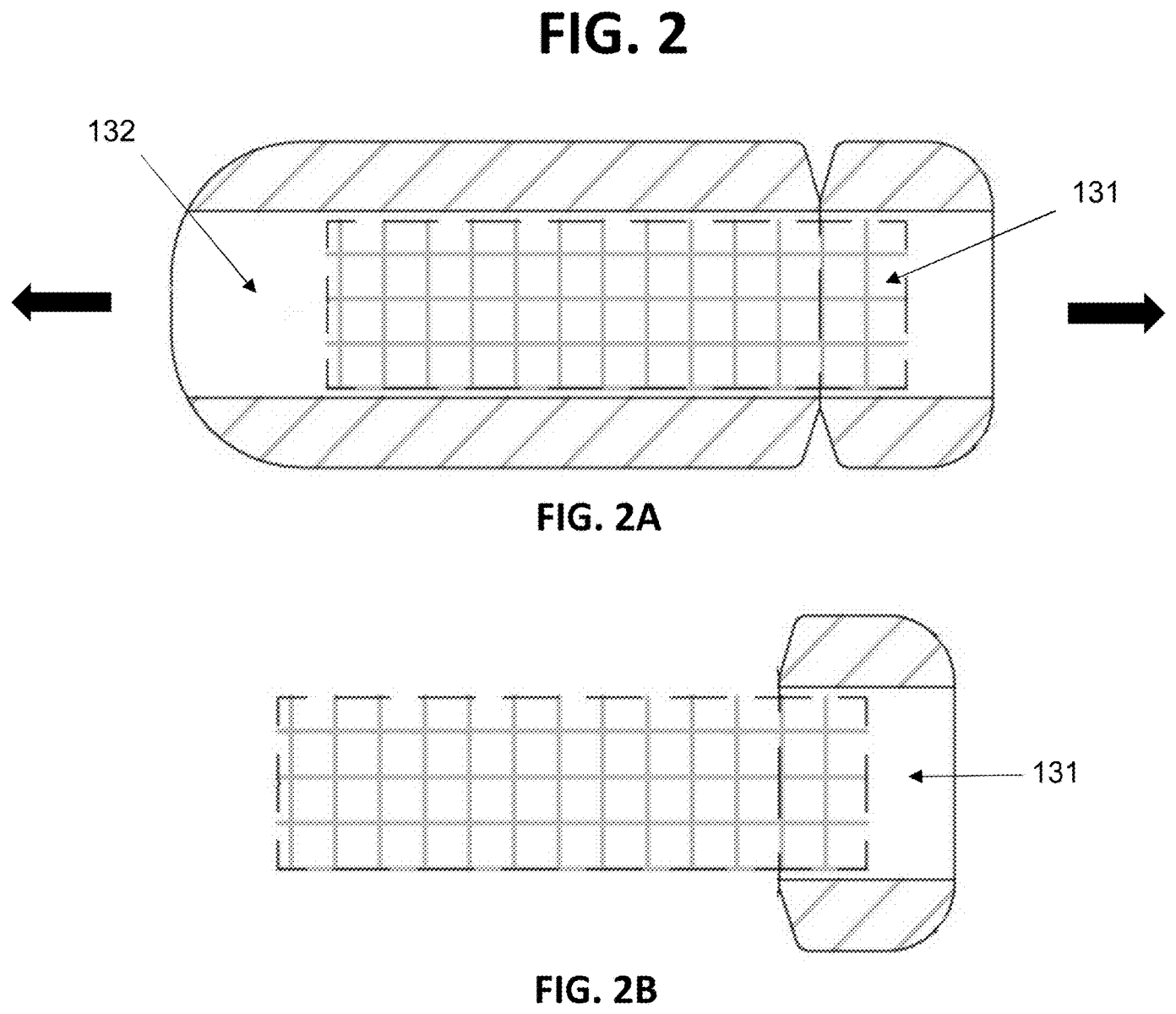
Figure 3:
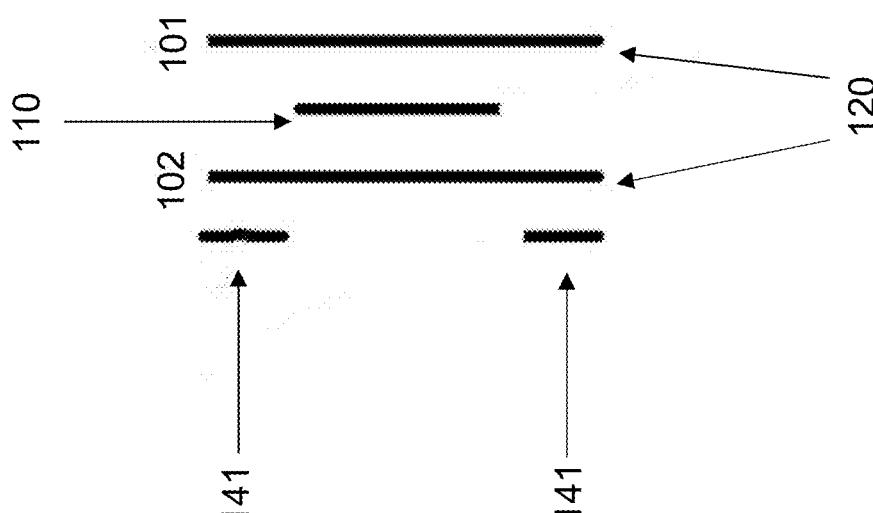
FIG. 3 is an illustration depicting front and side views of a mask insert. The side view depicts the layering and location of micro-hooks for attaching the mask insert to a mask.
Figure 3:
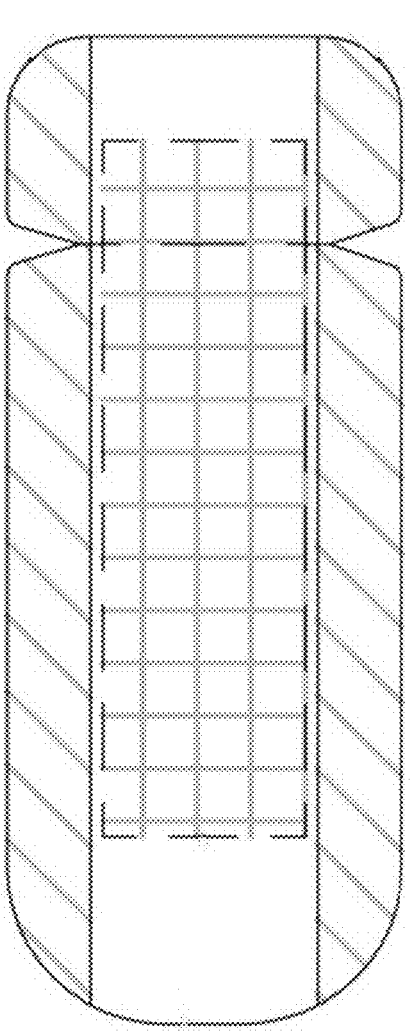

In one aspect, the present disclosure is directed to a mask insert. With reference to FIGS. 1-3, the mask insert includes first outer layer, a test substrate, and a second outer layer. One of the first layer or the second layer is oriented toward (proximal) to the subject's face and the other layer is coupled (attached) to the interior surface of a mask worn by the subject.

As illustrated in FIGS. 1-3, the first layer and the second layer have wider and longer dimensions than the test substrate (shown with hash marks with its outer border in dashed lines) and collectively form an outer layer. The outer edges (shown as diagonal lines "I") where the first layer and the second layer overlap each other, but do not overlap the test substrate, are bonded together to form an envelope or sleeve that surrounds the test substrate. The side view depicted in FIG. 3 illustrates how the inner test substrate 110 has slightly smaller dimensions than the outer layers. The side view shows the front of device 101, back of device 102, outer protective layers 120, and inner test substrate 110. FIG. 3 also illustrates the location of fasteners (e.g., micro-hooks 141 in the embodiment illustrated in FIG. 3) on the outer layer 120 surface that is distal from the subject's face and function to attach the mask insert to a mask worn by the subject. The overlapping ends of the first layer and the second layer are also bonded to each other (referred to in FIGS. 1 and 2 as "pinch point"). Bonding of the edges of the first layer and the second layer also creates a barrier that blocks or substantially reduces air from traveling through the first layer and the second layer and around the test substrate. Thus, bonding of the first layer and the second layer directs air flow toward the test substrate. The outer layer also functions as a protective layer for the test substrate and allow the mask insert to be handled and manipulated without the test substrate being directly contacted. The outer layers include materials for capture of bio-aerosol sizes less than 100 microns by providing a bioaerosol bandpass. The outer layers include a very low pressure drop material that allows bio-aerosols to flow easily through to reach the test substrate. The outer layer allows bio-aersols to pass, while not allowing macro contaminants to touch the inner test substrate, including RNAses and Proteases, which can degrade the analyte. The mask insert acts like a bandpass filter for allowing the larger bioaerosols to pass through the outer layers while the analyte is captured by the test substrate.

The edges of the mask insert have strips of microhook or adhesive along the edges that allow for the mask insert device to attach to any face cover material and be easily removed without damaging the face covering.

The outer layers are perforated along a line so that when the user pinches both ends and pulls the outer layers outward, the part of the outer layer is pulled away and can be disposed of. This exposes the inner capture substrate while allowing the user to still grip the outer substrate on one end without contaminating the capture substrate. The user can now place the inner substrate in a vial for testing.

The first layer and the second layer can be made of the same material or different material. Suitable material to make the first layer and second layer (and collectively the outer layer) includes, for example, spunbond polypropylene, spunbond polyester, meltblown fibers, carded nonwoven fibers, and the like. Particularly suitable material to make the first layer and second layer (and collectively the outer layer) includes 0.50 oz to 0.75 oz spunbound nonwoven coverweb material (commercially available from Barry Global, Evansvill, Indiana, USA). The materials of the first layer, the test substrate, and the second layer are designed to allow air expelled by the subject to pass through the first layer, the test substrate, and the second layer. The material of the first layer proximate to the subject's mouth and nose is also designed to allow an analyte contained in the air to pass through the first layer. The test substrate is designed to allow air to pass through (over) the test substrate but also capture the analyte contained in the air expelled by the subject. The second layer distal to the subjects face and proximal to the mask surface also allows air to flow out of the mask insert device. Suitable fiber size for materials for forming the outer layers have an average fiber diameter ranging from of about 5 micrometers to about 25 micrometers, including a range from about 10 micrometers to about 20 micrometers.

As illustrated in FIGS. 1-3, the mask insert 100 preferably includes a notch 190 in the outer layer proximate to one end of the mask insert that allows for easier separation and removal of a portion of the outer layer. As also illustrated in FIG. 1, the first layer and the second layer include perforations 191 that allow for easier separation and removal of the portion of the outer layer from the test substrate. Preferably, the notch is made in the outer substrate with the point ending with the beginning of the perforation. The right-side pinch point 131 and left-side pinch point 132 are occluded areas formed by protective back and front outer layers to block airflow from going around inner capture substrate layer 110. Micro-hooks 141 are able to stick to any face covering and occlude air from going around capture substrate. As further illustrated in FIG. 2, separation of the portion of the outer layer exposes the test substrate. FIG. 2A is a view before removing the outer protective layers. FIG. 2B is a view after removing the outer protective layers. When both ends of the mask insert are held and pulled outward, the portion of the outer layer is pulled away to expose the test substrate contained within the outer layer while allowing the person to still grip the end of the mask insert by the remaining portion without contaminating the test substrate. The test substrate can then be processed to detect analyte captured on the test substrate. The portion of the mask insert that provided the sleeve in which the test substrate was housed can be disposed of following removal of the test substrate. This allows for an easy detachment of the outer substrate layers from the inner test substrate 110 with the user still holding on to one end.

Figure 4:
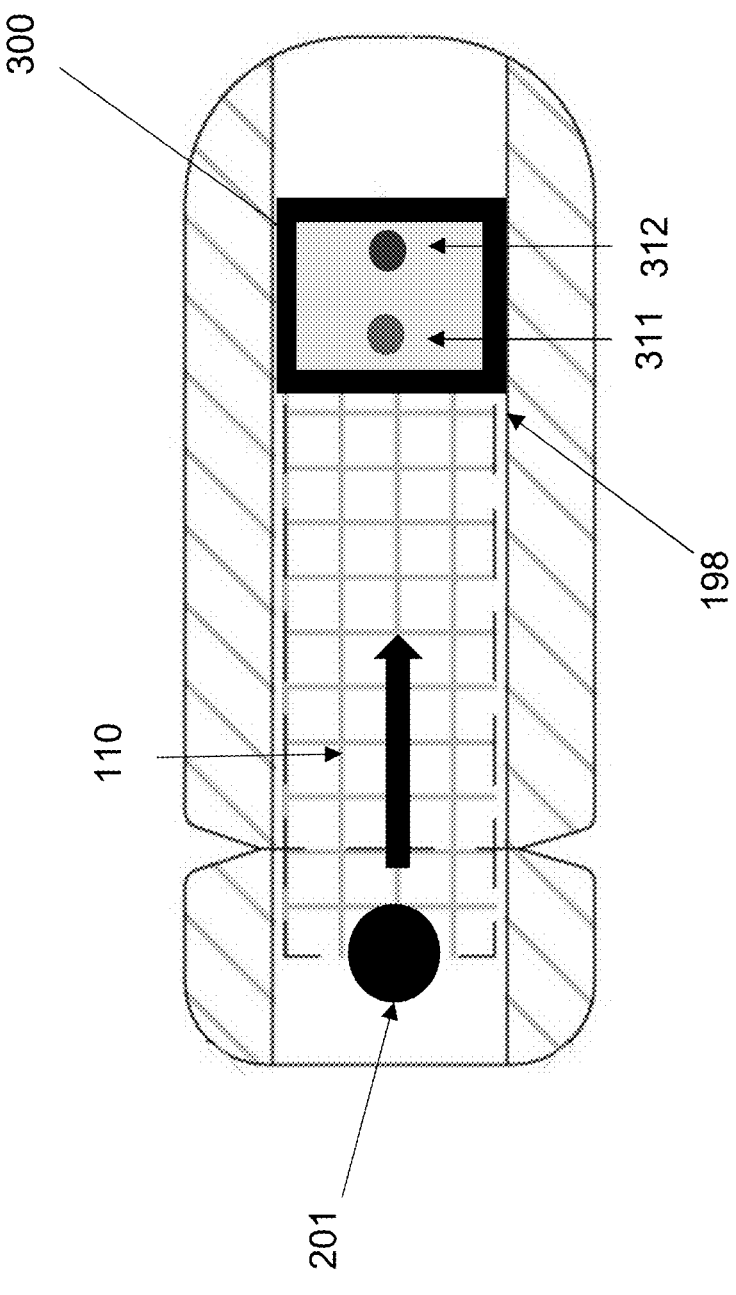
FIG. 4 is an illustration depicting a mask insert having a buffer well and with an integrated vertical flow assay.

In another aspect, the present disclosure is directed to a mask insert including an integrated vertical flow assay (VFA). FIG. 4 depicts an embodiment of a mask insert with an integrated vertical flow assay 300. As illustrated in FIG. 4, a buffer well 201 is positioned proximal to the notch and perforations for separating a portion of the outer layer as described herein. The well allows for a buffer that is added to the well to contact a portion of the inner test substrate. By capillary action, the buffer flows in a direction toward the vertical flow assay located distal to the buffer well. In the case where a charged material such as electret is used as the test substrate, the buffer shorts out the charges of the electret material as it flows toward the VFA, thereby transporting analytes and bio-markers to the VFA. The test substrate 110 can be made of a hydrophobic material and/or a material that is less hydrophilic than the VFA pad such that flow is toward the VFA. The test substrate contacts the VFA at a juncture 198 to allow the buffer with analytes to be transported to the VFA. The buffer can also include other biomarkers that serve as positive controls and/or negative controls and can also be detected by the VFA. The VFA portion of the mask insert can include a viewing "window" to allow the results of the VFA to be observed. FIG. 4 illustrates a test positive circle 311 and a test control circle 312 on the VFA.

Figure 5:
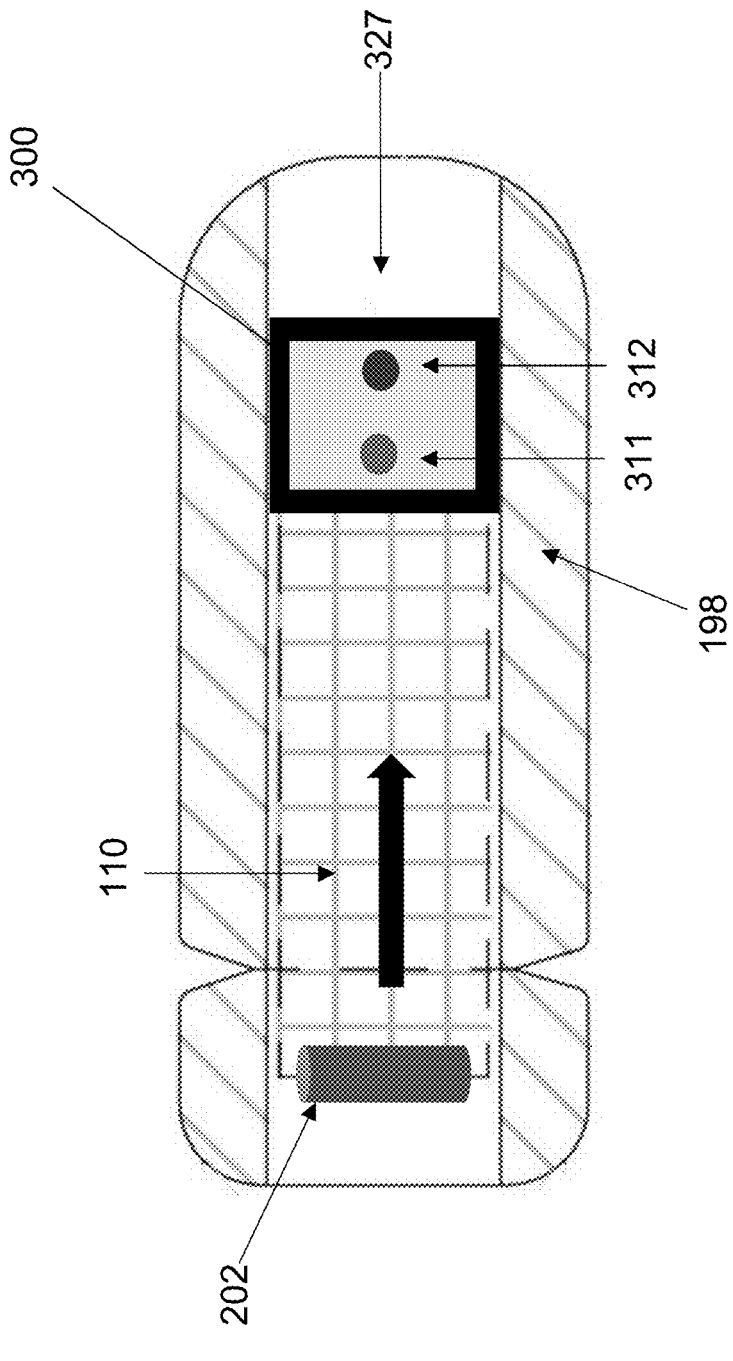
FIG. 5 is an illustration depicting a mask insert having a buffer dispensing device and with an integrated vertical flow assay.

FIG. 5 depicts an embodiment of a mask insert with integrated vertical flow assay 300 having a buffer dispensing device 202 positioned proximal to the notch and perforations depicted in FIG. 5. The buffer dispensing device provides an alternative to or an addition to a buffer well (depicted in FIG. 4). The buffer dispensing device can be an ampoule that is embedded into the interior of the mask insert. When a person applies pressure to the mask insert where the buffer dispensing device is positioned, all or a portion the buffer dispensing device ruptures to release the buffer contained in the buffer dispensing device. Through capillary action, the buffer flows in a direction toward the vertical flow assay located distal to the buffer dispensing device. In the case where a charged material such as electret is used as the test substrate 110, the buffer shorts out the charges of the electret material as it flows toward the VFA, thereby transporting analytes and bio-markers to the VFA. The test substrate can be made of a hydrophobic material and/or a material that is less hydrophilic than the VFA pad such that flow is toward the VFA. The test substrate contacts the VFA at a juncture 198 to allow the buffer with analytes to be transported to the VFA. The buffer can also include other biomarkers that serve as positive controls and/or negative controls and can also be detected by the VFA. The VFA portion of the mask insert can include a viewing "window" 327 to allow the results of the VFA to be observed. FIG. 5 illustrates a test positive circle 311 and a test control circle 312 on the VFA.

Figure 6:
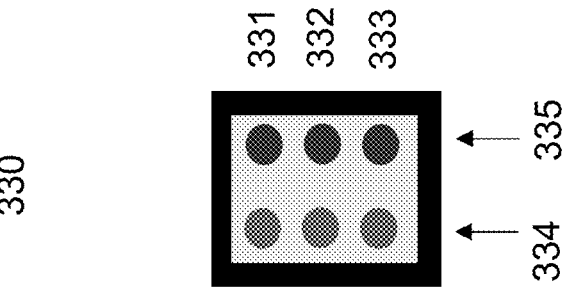
FIG. 6 is an illustration depicting a mask insert (with outer layer removed) having a buffer dispensing device and with an integrated vertical flow assay. Also depicted is a multiplex vertical flow assay platform.
Figure 6:
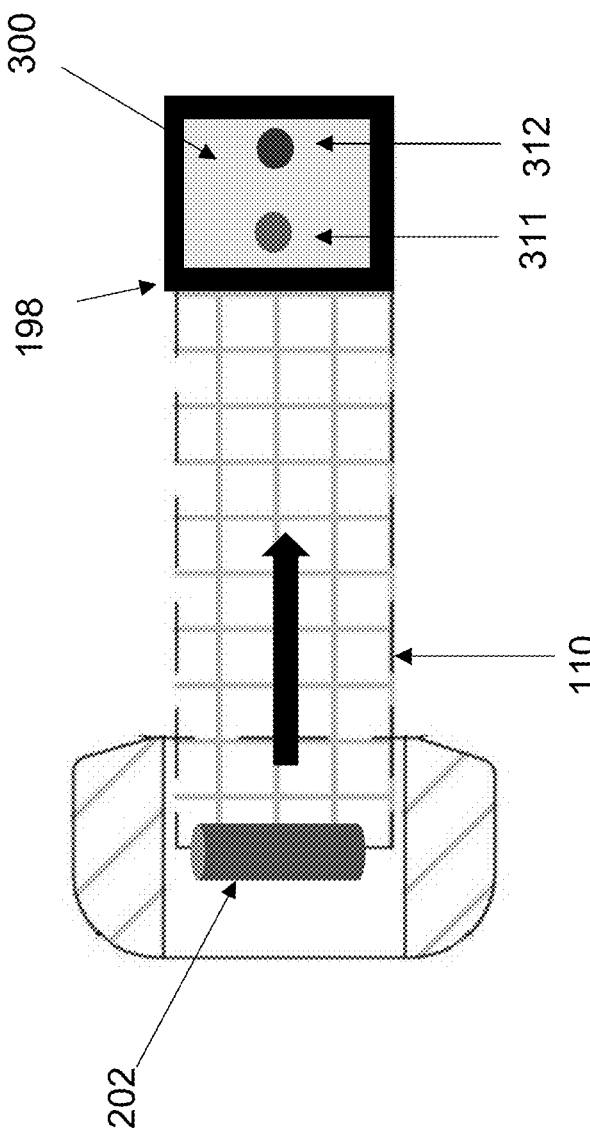

FIG. 6 depicts another embodiment of the mask insert illustrated in FIG. 5, but with a removable outer layer. FIG. 6 depicts a VFA 300 for single analyte detection and a VFA to perform multiplex testing 330 including test 1 (331), test 2 (332), and test 3 (333), and test positive circles 334 and test negative circles 335. Removal of the outer layer of the mask insert between the buffer dispensing device and the VFA permits the buffer to flow through the test substrate without also flowing into the material that forms the outer layer.

Figure 7:
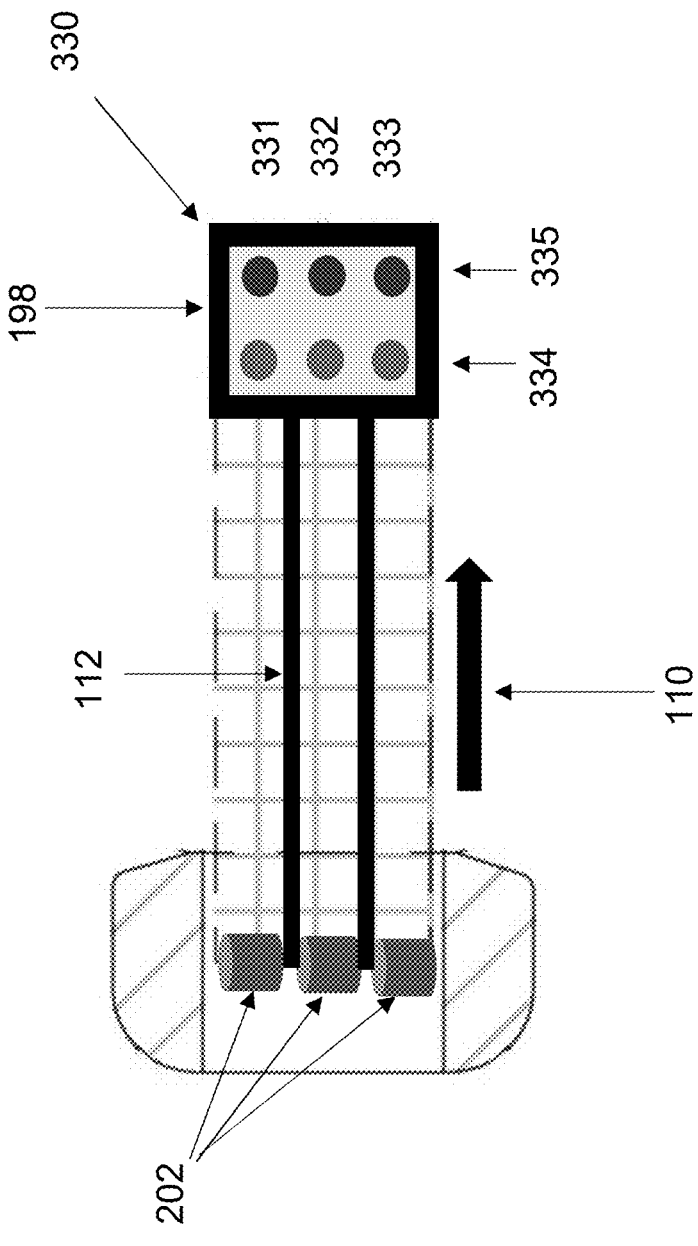
FIG. 7 is an illustration depicting a mask insert (with outer layer removed) having three buffer dispensing devices and with an integrated vertical flow multiplex assay.

In another embodiment, the mask insert can include two or more buffer dispensing devices. FIG. 7 depicts an exemplary embodiment of the mask insert that includes three buffer dispensing devices 202. The embodiment illustrated in FIG. 7 also includes a removable outer layer. Buffer from the buffer dispensing devices flows toward the VFA 330, but barriers 112 and/or occluded, non-porous spacing (or separations) in the test substrate allows for independent elution and extraction of the analyte from the test substrate "lanes" and prevent cross flow of each of the buffers into other "lanes" of the test substrate intended to detect a different analyte. Through capillary action, the buffer flows in a direction toward the vertical flow assay located distal to the buffer dispensing device. In the case where a charged material such as electret is used as the test substrate, the buffer shorts out the charges of the electret material as it flows toward the VFA, thereby transporting analytes and bio-markers to the VFA. The test substrate can be made of a hydrophobic material and/or a material that is less hydrophilic than the VFA pad such that flow is toward the VFA. Removal of the outer layer of the mask insert between the buffer dispensing device and the VFA permits the buffer to flow through the test substrate without also flowing into the material that forms the outer layer. The test substrate contacts the VFA to allow the buffer with analytes to be transported to the VFA. The buffer can also include other biomarkers that serve as positive controls and/or negative controls and can also be detected by the VFA. The VFA portion of the mask insert can include a viewing "window" to allow the results of the VFA to be observed. FIG. 7 also depicts an exemplary embodiment for multiplex testing.

Figure 8:
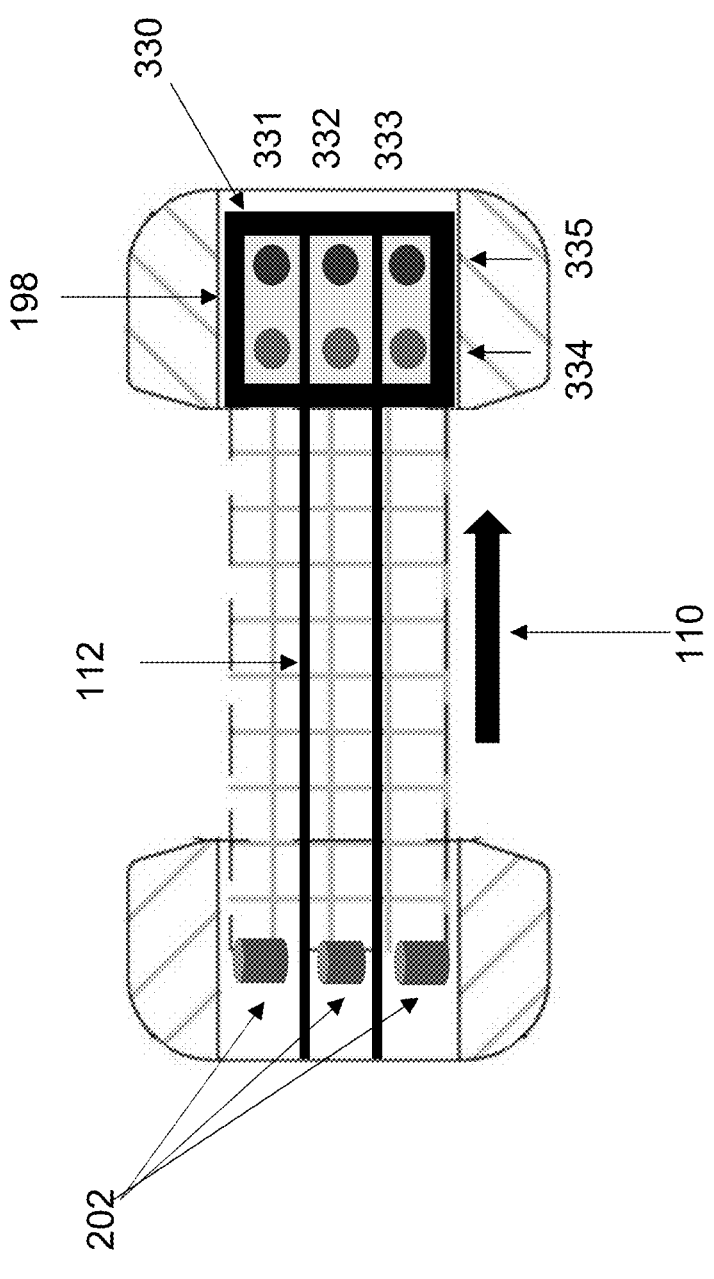
FIG. 8 is an illustration depicting a mask insert (with outer layer removed) having three buffer dispensing devices and with an integrated vertical flow multiplex assay.

FIG. 8 depicts another exemplary embodiment of the mask insert that includes three buffer dispensing devices. The embodiment depicted in FIG. 8 also includes perforations proximal to the buffer dispensing devices 202 and proximal to the VFA 330 to allow for removal of only the outer layer that surrounds the central portion of the test substrate 110. Buffer from the buffer dispensing devices 202 flows toward the VFA, but barriers and/or spacing 112 (or separations) in the test substrate prevent cross flow of each of the buffers into the test substrate 110. The occluded, non-porous spacing 112 allows for independent elution and extraction pathways for multiplexed testing of different analytes. The buffers do not cross the occlusion. Through capillary action, the buffer flows in a direction toward the vertical flow assay located distal to the buffer dispensing device. In the case where a charged material such as electret is used as the test substrate, the buffer shorts out the charges of the electret material as it flows toward the VFA, thereby transporting analytes and bio-markers to the VFA. Removal of the outer layer of the mask insert between the buffer dispensing device and the VFA permits the buffer to flow through the test substrate without also flowing into the material that forms the outer layer. The test substrate can be made of a hydrophobic material and/or a material that is less hydrophilic than the VFA pad such that flow is toward the VFA. The test substrate contacts the VFA to allow the buffer with analytes to be transported to the VFA. The buffer can also include other biomarkers that serve as positive controls and/or negative controls and can also be detected by the VFA. The VFA portion of the mask insert can include a viewing "window" to allow the results of the VFA to be observed. FIG. 8 also depicts an exemplary embodiment for multiplex testing.

In another embodiment, the mask insert includes an integrated vertical flow assay and at least one integrated delivery plunger to introduce a buffer to the test substrate.

Figure 9A:
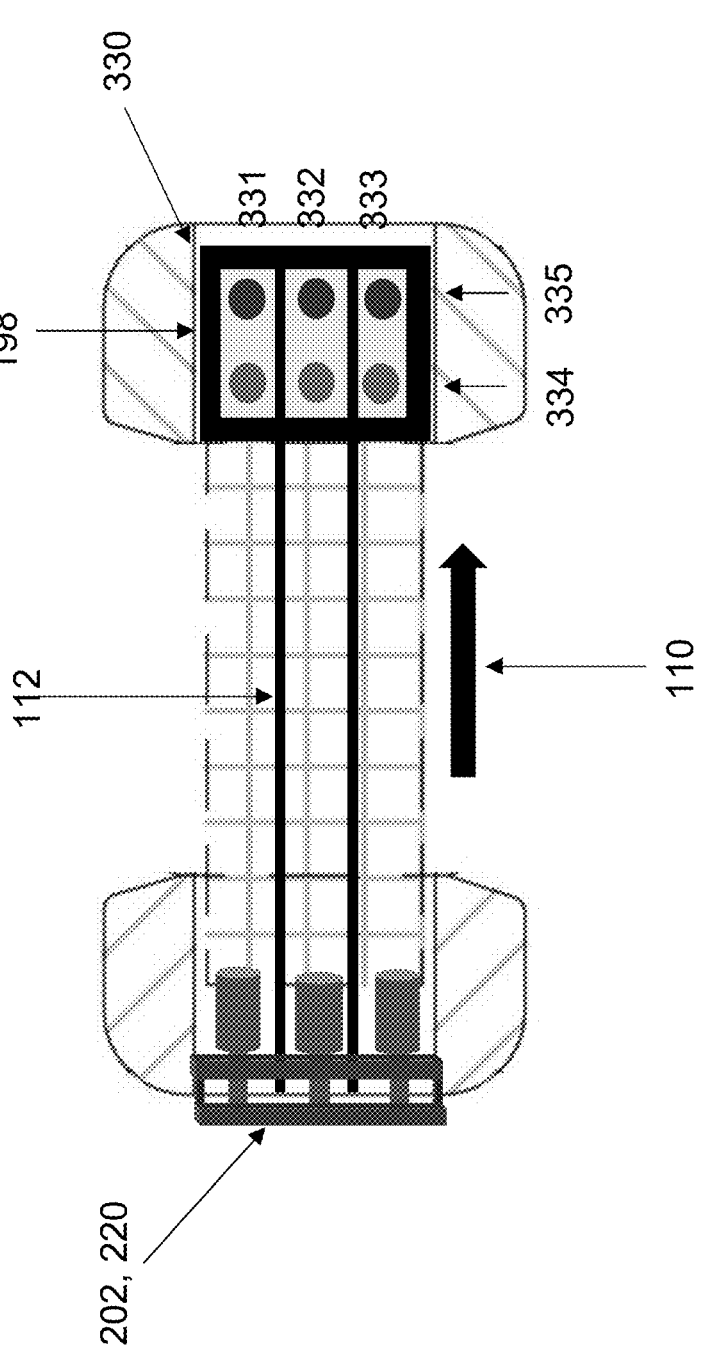
FIG. 9A is an illustration depicting a mask insert (with outer layer removed) having three buffer dispensing plunger devices and with an integrated vertical flow multiplex assay.
Figure 9B:
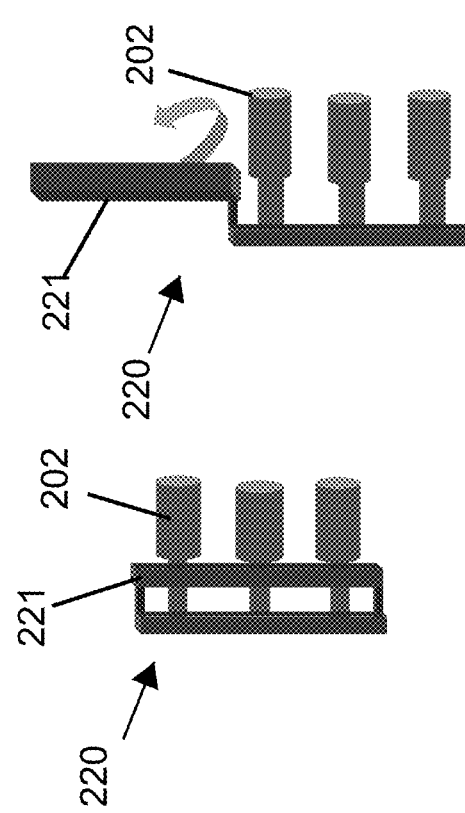
FIG. 9B is an illustration depicting an enlargement of the three buffer dispensing plunger devices.

FIG. 9A depicts an exemplary embodiment having three integrated delivery plungers 220. FIG. 9B depicts the delivery plunger 220. The vertical bar (locking bar 221) on the right is a locking mechanism that can be flipped up to allow the plunger on left side to be depressed to expel buffers from the plunger cavity to the test substrate.

Figure 10:
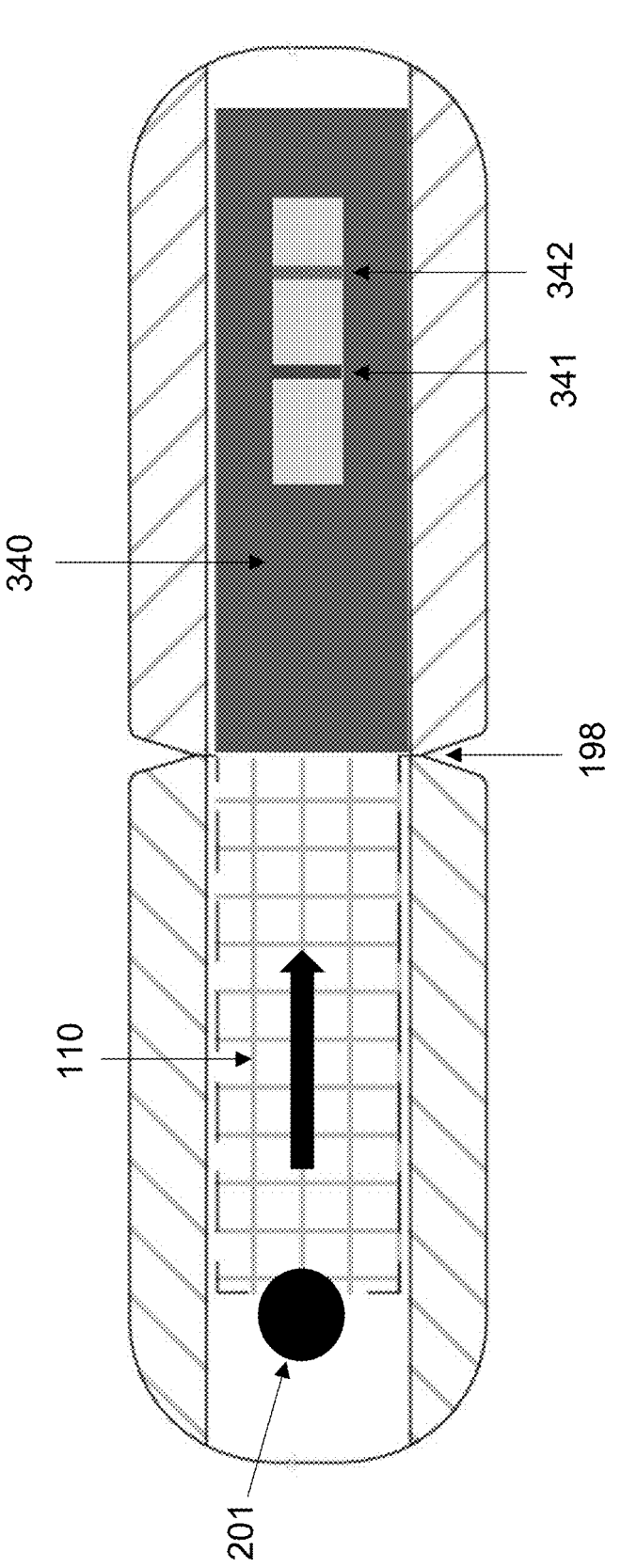
FIG. 10 is an illustration depicting a mask insert (with outer layer in place) having a buffer well and with an integrated lateral flow assay.

In another embodiment, the mask insert includes an integrated lateral flow assay. FIG. 10 depicts an exemplary embodiment of a mask insert with an integrated lateral flow assay (LFA) 340. The embodiment of FIG. 10 includes a well 201 for introducing buffer to extract and/or elute analytes and transport analytes from the test substrate toward the lateral flow assay sample pad. The buffer flow shorts out electret charges as it flows toward the LFA sample pad, thereby transporting pathogen and bio-markers in the buffer for testing. The test substrate 110 can be made of a hydrophobic material and/or a material that is less hydrophilic than the LFA pad. As depicted in FIG. 10, the test substrate 110 is in contact with the sample pad of the LFA 340 at a juncture 198. FIG. 10 shows a test positive line 341 and a test control 342. The LFA can be integrated with the mask insert in the form of a standard LFA cassette or as a laminated LFA. The embodiment depicted in FIG. 10 is also capable of use for multiplex testing.

Figure 11:
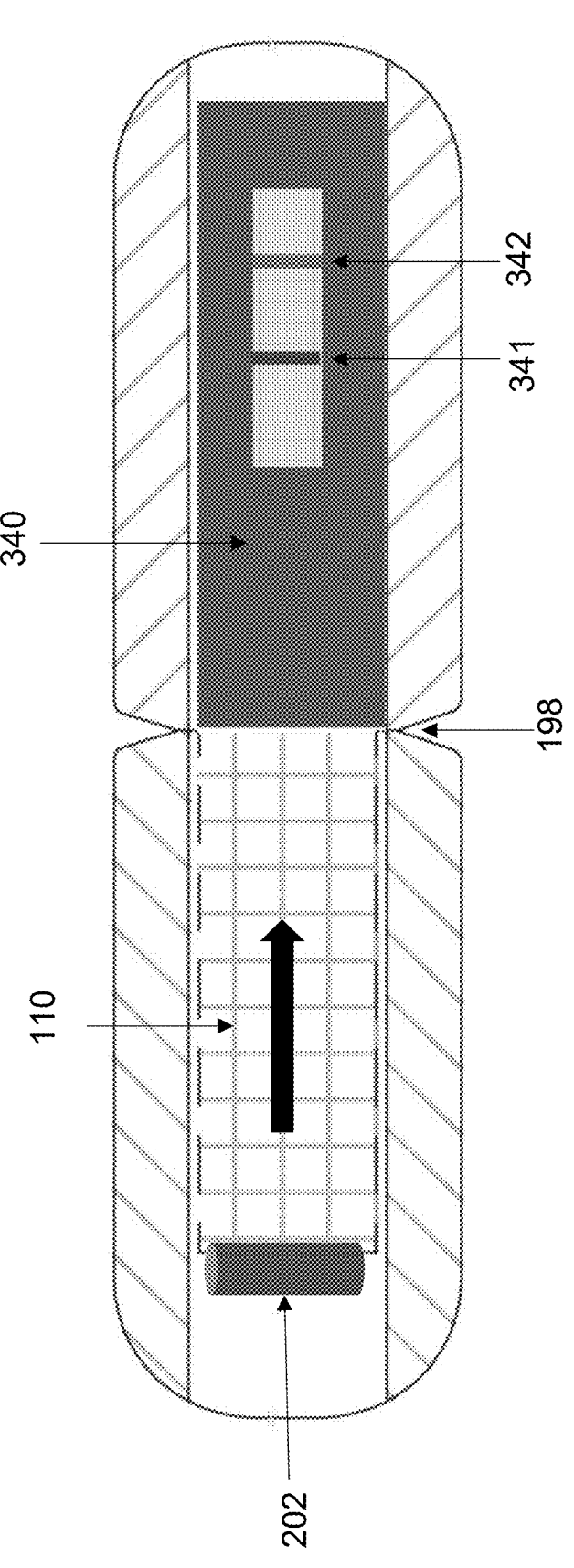
FIG. 11 is an illustration depicting a mask insert (with outer layer in place) having a buffer dispensing device and with an integrated lateral flow assay.

In another embodiment depicted in FIG. 11, the mask insert includes an integrated lateral flow assay 340 further including a buffer dispensing device 202 (ampoule) for introducing buffer to extract and/or elute analytes and transport analytes from the test substrate toward the lateral flow assay 340 sample pad. As discussed herein, pressure applied to the buffer dispensing device releases the buffer that flows through capillary action through the test substrate toward the LFA. The buffer flow shorts out electret charges as it flows toward the LFA sample pad, thereby transporting analyte and bio-markers in the buffer for testing. The test substrate 110 can be made of a hydrophobic material and/or a material that is less hydrophilic than the LFA pad. As depicted in FIG. 11, the test substrate 110 is in contact with the sample pad of the LFA 340 at a juncture 198. FIG. 11 shows a test positive line 341 and a test control 342. The LFA can be integrated with the mask insert in the form of a standard LFA cassette or as a laminated LFA. The embodiment depicted in FIG. 11 is also capable of use for multiplex testing.

Figure 12:
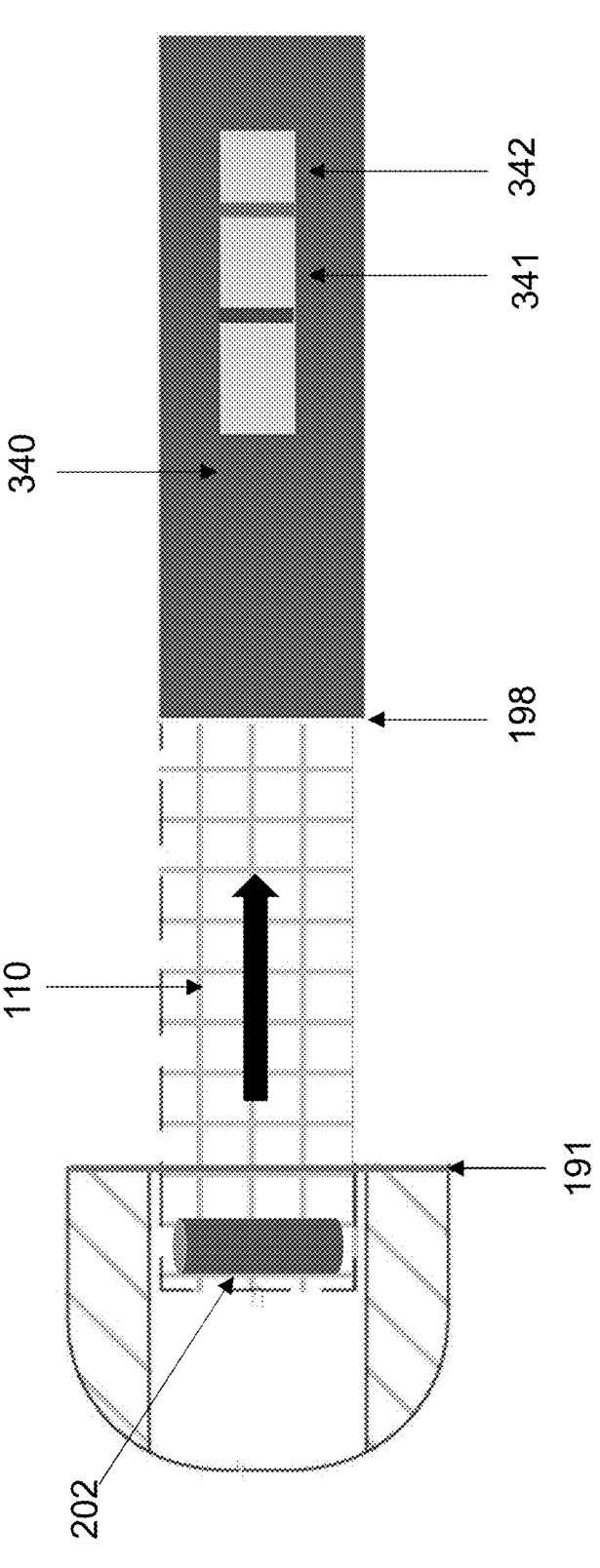
FIG. 12 is an illustration depicting a mask insert (with outer layer removed) having a buffer dispensing device and with an integrated lateral flow assay.
Figures 13A, 13B, 13C:
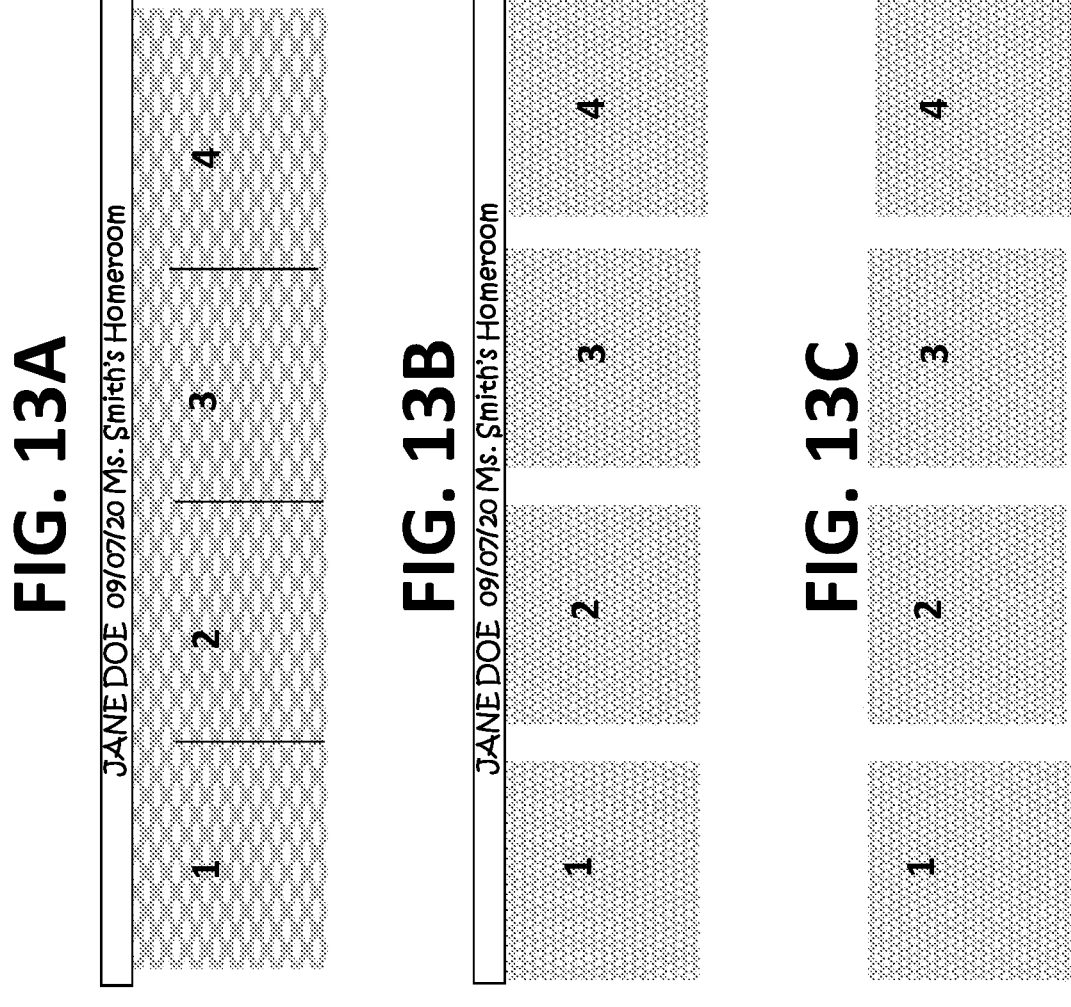
FIGS. 13A-13C depict exemplary embodiments of test substrates illustrating tabs.
Figure 14:
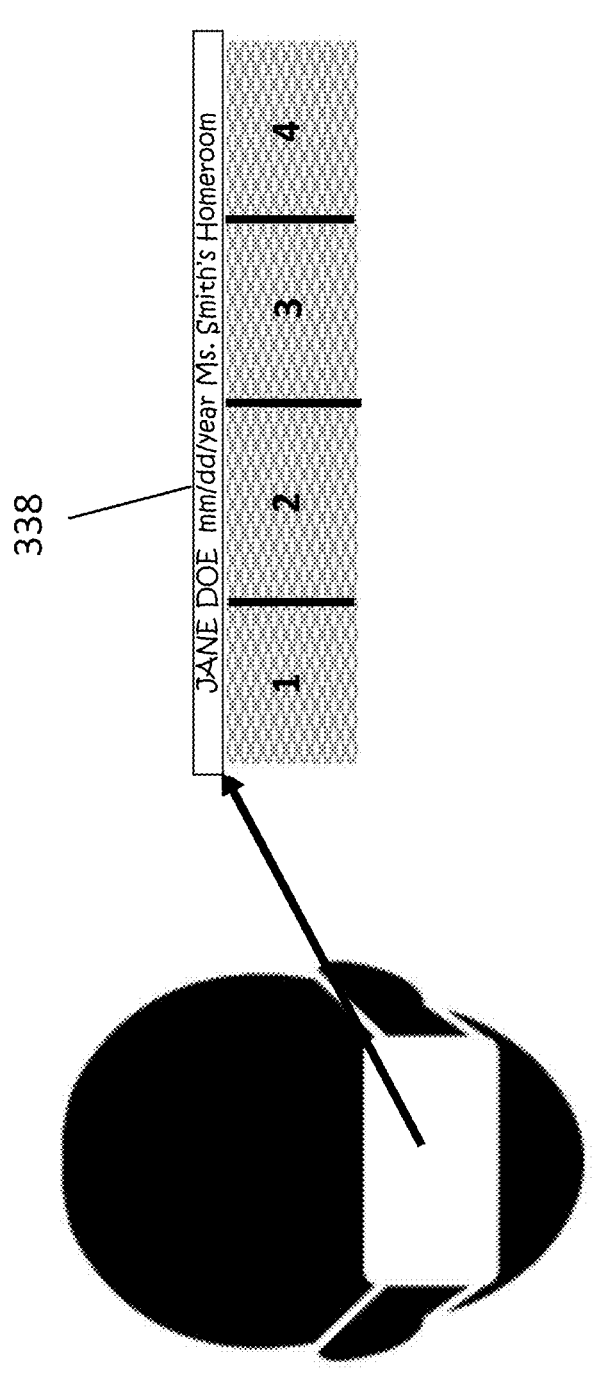
FIG. 14 depicts the embodiment of FIG. 13 as part of a face mask worn by a user, showing a multi-test device strip 338.
Figure 15:
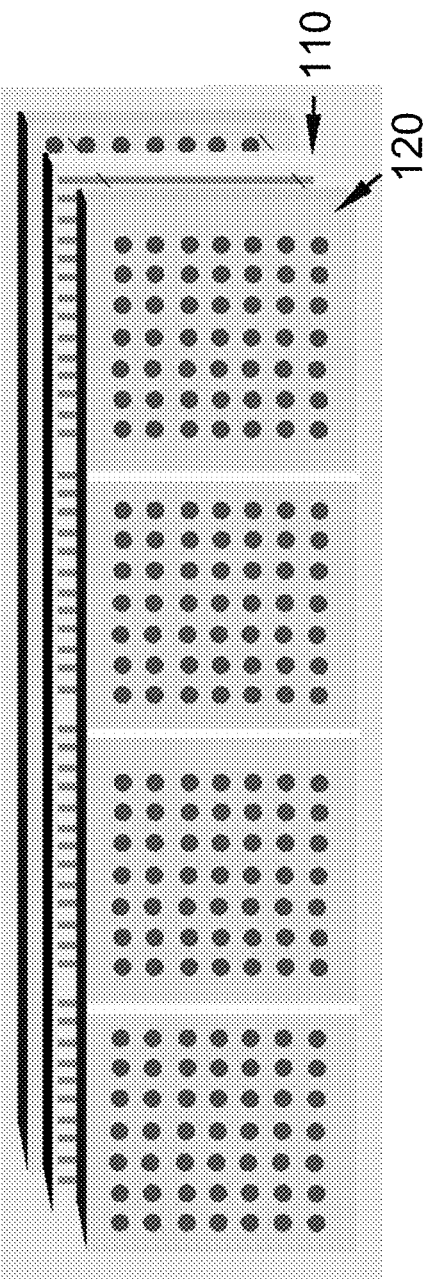
FIG. 15 depicts an exemplary embodiment of a multi-layer test substrate having 4 tab portions, an inner test substrate that is protected on all sides and is made of a material having high surface area that can be released from the outer protective layers.
Figure 16:
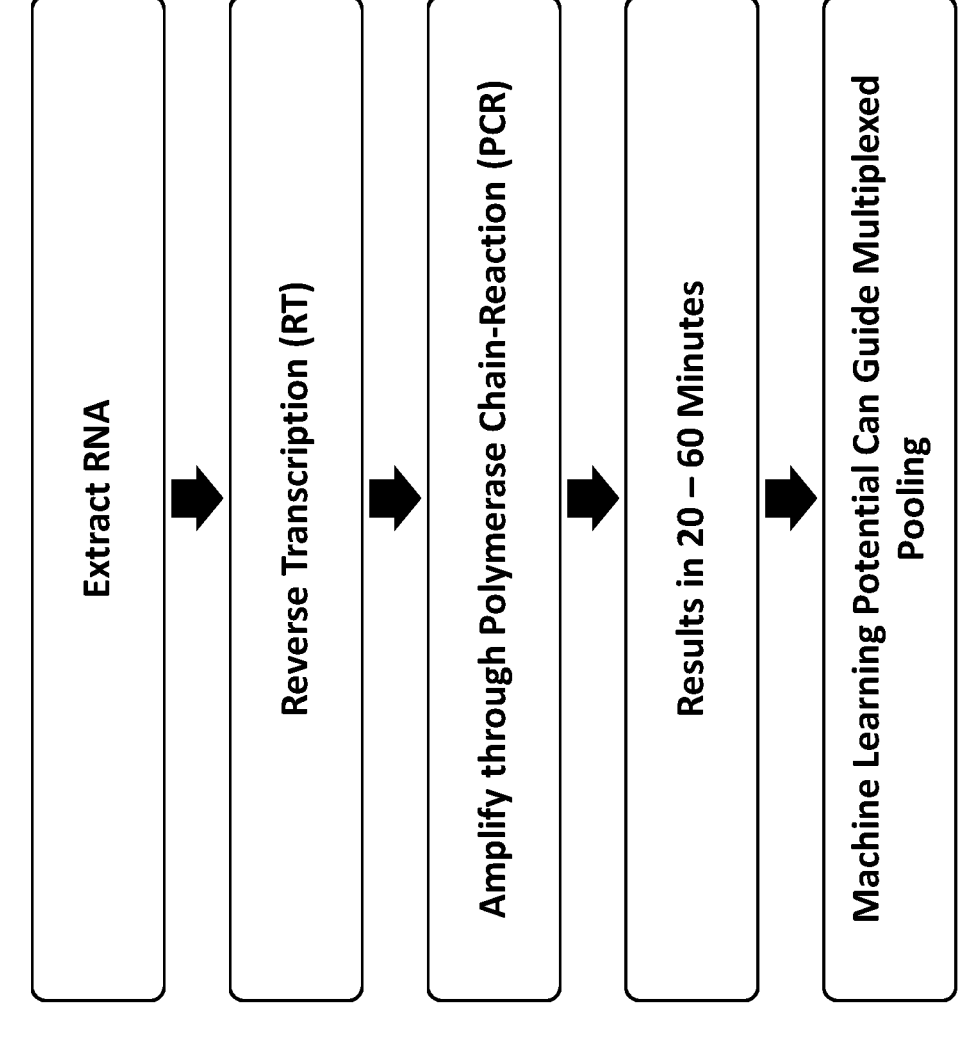
FIG. 16 depicts a flow diagram for extraction and amplification of RNA from the test substrate.

In another exemplary embodiment depicted in FIG. 12, the mask insert includes an integrated lateral flow assay 340 further including a buffer dispensing device 202 (ampoule) for introducing buffer to extract and/or elute analytes and transport analytes from the test substrate toward the lateral flow assay 340 sample pad. As discussed herein, pressure applied to the buffer dispensing device releases the buffer that flows through capillary action through the test substrate toward the LFA. The buffer flow shorts out electret charges as it flows toward the LFA sample pad, thereby transporting analyte and bio-markers in the buffer for testing. The test substrate 110 can be made of a hydrophobic material and/or a material that is less hydrophilic than the LFA pad. Removal of the outer layer of the mask insert between the buffer dispensing device and the LFA permits the buffer to flow through the test substrate without also flowing into the material that forms the outer layer. Perforations 191 in perforated front and back outer layers allow for easy removal to ensure to inhibition of flow by outer layers. As depicted in FIG. 12, the test substrate is in contact with the sample pad of the LFA. The LFA can be integrated with the mask insert in the form of a standard LFA cassette or as a laminated LFA. The embodiment depicted in FIG. 12 is also capable of use for multiplex testing.

The test substrate is designed to capture an analyte in an air sample from a subject. In some embodiments, the test substrate has a pore size that is smaller than the size of analytes. In other embodiments, the test substrate is made of a material that attracts analytes. In some embodiments, the test substrate has a pore size that is smaller than the size of the analyte and is also made of a material that attracts the analyte. Pore size for capturing analytes is less than 100 microns. A particularly suitable pore size for capturing analytes such as pathogens is less than 75 microns, less than 50 microns, and less than 25 microns. Materials can be altered to target specific analytes while minimizing pressure drop. For instance, capturing COVID can require a higher pressure drop since a denser material is needed because COVID is smaller. TB can be caught at a similar efficiency with a less dense materials, therefore having a lower pressure drop and higher throughput. Exemplary analytes intended to be capturable by the test substrate of the mask insert include COVID-19 (approximately 100 nm), Influenza (approximately 80-120 nm); *Mycobacterium* (approximately 7 microns), other bio-aerosols containing respiratory pathogens (less than 10 microns). As described herein, the test substrate material can be treated (such as by imparting a charge to the material) to "attract" an analyte to the test substrate. Thus, for example, a less dense material can be treated to attract COVID to the test substrate as compared to an untreated material.

The mask insert is coupled (attached) to an inner surface of a mask. The mask insert is coupled to the mask surface by adhesives and other fasteners such as hook and loop fasteners. Preferably, the mask insert includes micro-hooks that allow the mask insert to attach to the inner surface of the mask worn by the subject. Other coupling mechanisms are also suitable. For example, the mask insert can be attached to the mask surface using adhesives. Generally, non-permanent adhesives are preferred such that the mask insert can be removed from the mask surface.

Air is expelled by the subject by breathing, coughing, sneezing, speaking, and combinations thereof.

In one embodiment, the mask insert is reversibly coupled to a mask worn by a user. As used herein, "reversibly coupled" refers to an ability to attach the mask insert to the mask, then remove the mask insert from the mask, and then reattach the mask insert to the mask. In some embodiments, the mask is reusable and a new mask insert is attached to the mask.

In another embodiment, the mask insert is semi-permanently coupled to a mask worn by a user. In this embodiment, the mask insert can be separated from the mask after being attached to the mask surface, but is not intended to be reattached to the mask insert after removal from the mask surface.

In another embodiment, the mask insert is permanently coupled to a mask worn by a user. In this embodiment, the mask insert is not intended to be separated from the mask once the mask insert is attached to the mask surface.

Generally, the mask insert (whether reversibly coupled or permanently coupled) is positioned on an inner surface of the mask where air expelled by the user by normal breathing, forceful breathing, coughing, sneezing and any combination thereof causes the air to flow to the mask insert.

As used herein, the substrate to be tested (also referred to interchangeably herein as the "test substrate" and the "collection substrate") can include any inanimate surface that can come into contact with an individual or groups of individuals that is capable of including pathogens on its exterior surface. For example, in one embodiment, the substrate to be tested can be an entire mask intact or from which a portion (i.e., the test substrate) of the mask is removed. The substrate can also include a removable mask insert. In some embodiments, the mask insert can be cleaned and reused by placing back into the mask.

In some embodiments, the test substrate is processed to extract and/or remove pathogen material from the test substrate. In other embodiments, testing does not require removal or extraction of the pathogen material from the test material. For example, a test substrate can be analyzed by placing it in a reaction solution (e.g., buffer and/or water) that results in a colorimetric reaction indicating the presence or absence of a pathogen. In another embodiment, the test substrate is placed in a reaction solution (e.g., buffer and/or water) whereby the test substrate dissolves. In another embodiment, a reagent is applied to the test substrate. In another embodiment, a reagent is contacted with the test substrate which draws the reagent into the test substrate by capillary action.

The test substrate can be suitably made with synthetic fibers, natural fibers, and combinations thereof. Fibers used to form layers can be hydrophobic fibers, hydrophilic fibers, and combinations thereof. Hydrophobic fibers include, for example, polylactones, poly(caprolactone), poly (L-lactic acid), poly (glycolic acid), similar co-polymers poly(alkyl acrylate), polybutadiene, polyethylene, polystyrene, polyacrylonitrile, polyethylene (terephthalate), polysulfone, polycarbonate, poly(vinyl chloride), and combinations thereof. Hydrophilic fibers include, for example, linear poly (ethylenimine), cellulose, cellulose acetate and other grafted cellulosics, poly (hydroxyethylmethacrylate), poly (ethyleneoxide), polyvinylpyrrolidone, poly(acrylic acid), poly (ethylene glycol), poly(vinyl alcohol), poly (vinyl acetate), poly(acrylamide), proteins, poly (vinyl pyrrolidone), poly (styrene sulfonate), and combinations thereof. Other suitable fiber materials include, for example, acrylonitrile/butadiene copolymer, cellulose, cellulose acetate, chitosan, collagen, DNA, fibrinogen, fibronectin, nylon, poly(acrylic acid), poly (chloro styrene), poly(dimethyl siloxane), poly(ether imide), poly(ether sulfone), poly(ethyl acrylate), poly(ethyl vinyl acetate), poly(ethyl-co-vinyl acetate), poly(ethylene oxide), poly(ethylene terephthalate), poly(lactic acid-co-glycolic acid), poly(methacrylic acid) salt, poly(methyl methacrylate), poly(methyl styrene), poly(styrene sulfonic acid) salt, poly(styrene sulfonyl fluoride), poly(styrene-co-acrylonitrile), poly(styrene-co-butadiene), poly(styrene-co-divinyl benzene), poly(vinyl acetate), poly(vinyl alcohol), poly(vinyl chloride), poly(vinylidene fluoride), polyacrylamide, polyacrylonitrile, polyamic acid (PAA), polyamide, polyaniline, polybenzimidazole, polycaprolactone, polycarbonate, polydimethylsiloxane-co-polyethyleneoxide, polyetheretherketone, polyethylene, polyethyleneimine, polyimide, polyisoprene, polylactide, polypropylene, polystyrene, polysulfone, polyurethane, polyvinylpyrrolidone, proteins, SEBS copolymer, silk, styrene/isoprene copolymer, and combinations thereof. Polymer blends such as, for example, poly(vinylidene fluoride)-blend-poly(methyl methacrylate), polystyrene-blend-poly(vinylmethylether), poly(methyl methacrylate)-blend-poly(ethyleneoxide), poly (hydroxypropyl methacrylate)-blend poly(vinylpyrrolidone), poly(hydroxybutyrate)-blend-poly(ethylene oxide), protein blend-polyethyleneoxide, polylactide-blend-polyvinylpyrrolidone, polystyrene-blend-polyester, polyester-blend-poly(hyroxyethyl methacrylate), poly(ethylene oxide)-blend poly(methyl methacrylate), poly(hydroxystyrene)-blend-poly(ethylene oxide), and combinations thereof.

Another suitable layer of the test substrate can be electret (including thermoelectrets and fibrillated electret film). Electret is a dielectric material having a quasi-permanent electric charge or dipole polarization. Electret can be obtained from commercially available sources. Electret can be prepared by heating and simultaneously exposing a material to an electric field, whereby many dipoles in the material become oriented in a preferred direction. After the heating, the material is "frozen" and is able to keep the position of its electric dipoles for a long period of time. Suitable materials for preparing electrets include, for example, materials can now be used to fabricate thermoelectrets, including organic materials such as ebonite, naphthalene, polymethyl-methacrylate, and many polymers, and inorganic materials such as sulfur, quartz, glasses, steatite, and some ceramics. Electret fibrous membranes are particularly suitable. Polyvinylidene fluoride (PVDF)/polytetrafluoroethylene (PTFE) NP electret nanofiber membranes can be formed by electrospinning. Fibrillated electret film as described in Van Turnhout (U.S. Pat. No. 3,998,916) is also suitable.

Particularly suitable test substrates are charged materials (e.g., polypropylene, polylactic acid, and electret) that attracts analytes contained in the air sample. Thus, analytes contained in the air of a subject are not necessarily trapped by the test substrate because of a size difference between the test substrate and the analyte, but are attracted to the test substrate.

Embodiments using polypropylene as the test substrate advantageously provide an inert substrate that allows biological materials such as pathogens to be stable for long periods of time, including when the mask insert and/or test substrate requires transport for testing. The test substrate can also include coatings and chemical treatments that allow for easier elution of analytes. Lower surface energy materials can be used to increase the wetting capability of the test substrate materials so less buffer is required to wet-out the material, and therefore, concentrate the analyte in the eluted buffer. Hydrophobic polypropylene has an advantage of easily discharging and allowing the elution of virions from the nonwoven with a simple application of a buffer such as 0.1% Triton X-100, which and performs a crude extraction with certain pathogens, such as SARS-CoV-2.

The test substrate material can also be treated to impart electric charge, to make the material more or less hydrophilic, to make the material more or less hydrophobic, and combinations thereof.

Suitable test substrate materials also include materials that are dissolvable and/or soluble in a liquid. For example, cellulose acetate nanofibers that are capable of dissolution upon contact with a liquid. It should be understood that the entire test substrate and/or portions thereof (e.g., collection substrates) can be dissolvable or soluble. Advantageously, the substrate itself can dissolve completely freeing all analyte material into the eluent without requiring a removal process. Suitably, the substrate can be made when the substrate dissolves, it reacts and stabilizes RNA or performs some other service detection. Suitably, the substrate may be inert before it is dissolved. Additionally, or alternatively, the protective inert layer of inner substrate that dissolves revealing a less inert, active inner substrate that has active diagnostic properties. For example, a test substrate (such as a rod) is placed in eluent that dissolves outer coating releasing full amount of viral material. The test reagent then dissolves and interacts with analyte material.

Fibers can be sub-nanofibers, nanofibers, microfibers, and combinations thereof, having diameters ranging from subnanometers to micrometers. Sub-nanofibers can be prepared using template assisted growth, oriented attached growth, ligand controlled growth, and catalyst-guided growth. Sub-nanometer fibers (also referred to herein as "sub-nanofibers") refer to the one dimensional structure with ultrahigh aspect ratio with the diameter ranging from several angstroms to dozens of angstroms. Ultrathin nanofibers with the diameter of less than 100 nm can be produced by phase separation, self-assembling, sea-island method, template synthesis, electrospinning, and bubble-electrospinning. Nanofiber diameter ranges include, for example, about 3 nm to less than 1 μm. Microfiber diameter ranges include, for example, from 1 μm to about 10 μm. Nanofiber and microfibers can be produced using phase separation, self-assembling, sea-island method, template synthesis, electrospinning, and bubble-electrospinning, melt-blowing, spin-blowing, and other methods. Fiber diameter and morphology can be determined using scanning electron microscopy (SEM), transmission electron microscopy (TEM), and atomic force microscopy (AFM). The test substrate fibers can be woven, knitted, crocheted, knotted, pressed together, interlaced, bonded, stapled together in the form of a sheets webs, and combinations thereof. Layers can be formed using spun-bonded materials prepared with continuous fibers formed by continuously extruding a polymer through a spinnerette to form discrete filaments. Filaments can then be mechanically or pneumatically drawn without breaking to orient the polymer filaments. The continuous filaments can be deposited in a substantially random manner onto a carrier belt to form a web. Layers can also be formed using melt-blown fibers. Layers can also be formed using electrospun fibers. As known to those skilled in the art, electrospinning involves drawing individual polymer chains in a polymer solution as nano- or submicroscaled structures in form of fibers under high voltage typically through a nozzle/ orifice with a very small diameter.

Additives can be included with the test substrate layers. Suitable additives include, for example, antimicrobial additives such as silver-containing antimicrobial agents and antimicrobial polypeptides, analgesic compounds such as lidocaine, antibiotics such as neomycin, thrombogenic compounds, nitric oxide releasing compounds such as sydnonimines and NO-complexes, bacteriocidal compounds, fungicidal compounds, bacteriostatic compounds, other pharmaceutical compounds, adhesives, fragrances, odor absorbing compounds, preservatives, RNAse inhibitors, protease inhibitors, and nucleic acids, including deoxyribonucleic acid, ribonucleic acid, and nucleotide analogs.

Suitable analytes are contained in gases and aerosol droplets in air expelled by the user. Suitable analytes include microorganisms, chemicals, proteins, nucleic acids, and combinations thereof. Suitable microorganisms include bacteria and viruses.

Particularly suitable microorganisms include pathogens. The term "pathogen" is used according to its ordinary meaning to refer to bacteria, viruses, and other microorganisms that directly or indirectly cause disease. Exemplary pathogens include, for example, *Yersinia, Klebsiella, Providencia, Erwinia, Enterobacter, Salmonella, Serratia, Aerobacter, Escherichia, Pseudomonas, Shigella, Vibrio, Aeromonas, Streptococcus, Staphylococcus, Micrococcus, Moraxella, Bacillus, Clostridium, Corynebacterium, Eberthella, Francisella, Haemophilus, Bacteroides, Listeria, Erysipelothrix, Acinetobacter, Brucella, Pasteurella, Flavobacterium, Fusobacterium, Streptobacillus, Calymmatobacterium, Legionella, Treponema, Borrelia, Leptospira, Actinomyces, Nocardia, Rickettsia, Micrococcus, Mycobac-*

*terium, Neisseria, Campylobacter*, pathogenic viruses such as, for example, Papilloma viruses, Parvoviruses, Adenoviruses, Herpesviruses, Vaccine virus, Arenaviruses, Coronaviruses, Rhinoviruses, Respiratory syncytial viruses, Influenza viruses, Picornaviruses, Paramyxoviruses, Reoviruses, Retroviruses, Rhabdoviruses, human immunodeficiency virus (HIV), *Taenia, Hymenolepsis, Diphyllobothrium, Echinococcus, Fasciolopsis, Heterophyes, Metagonimus, Clonorchis, Fasciola, Paragonimus, Schistosoma, Enterobius, Trichuris, Ascaris, Ancylostoma, Necator, Wuchereria, Brugi, Loa, Onchocerca, Dracunculus, Naegleria, Acanthamoeba, Plasmodium, Trypanosoma, Leishmania, Toxoplasma, Entamoeba, Giardia, Isospora, Cryptosporidium, Enterocytozoa, Strongyloides, Trichinella*, a fungus causing, for example, Ringworm, Histoplasmosis, Blastomycosis, Aspergillosis, Cryptococcosis, Sporotrichosis, Coccidiodomycosis, Paracoccidioidomycosis, Mucomycosis, Candidiasis, Dermatophytosis, Protothecosis, *Pityriasis*, Mycetoma, Paracoccidiodomycosis, Phaeohphomycosis, Pseudallescheriasis, Trichosporosis, *Pneumocystis*, and combinations thereof.

Particularly suitable chemicals include ketones, nicotine, cocaine, opioids, marijuana, benzodiazepines, amphetamines, barbiturates, and combinations thereof.

Proteins, DNA, and RNA can also be detected.

Suitable masks include any face covering worn over or in front of a user's mouth and nasal passage where air passes out of the user during, for example, exhalation, when speaking, coughing, and sneezing. The mask can be secured to the user's face using ties, straps, bands, and combinations thereof. Masks also include face shields. Masks also include bandanas, neck gaiters, scarfs, towels and cloth coverings positioned over a user's nose and mouth. Thus, the mask inserts of the present disclosure can be coupled with any type of face covering such that at least a portion of air expelled (by breathing, coughing, sneezing, talking) passes to the device where analytes contained in the air sample can be collected by the test substrate.

When the analyte is a pathogen, the amount of pathogen particles captured can be expressed as a filtration efficiency, a minimum efficiency reporting value rating, and a microparticle performance rating. Suitably, the filtration efficiency of the test substrate ranges from about 60% to about 95%. Suitably, the minimum efficiency reporting value rating is at least 12. Suitably, the microparticle performance rating is at least 1900.

Any suitable method can be used for cleaning the mask and/or mask insert such as for example, washing and/or sterilization by heat treatment, ultra violet light irradiation, and other sterilization methods. In other embodiments, the mask and/or mask insert is a single-use mask or mask insert. In these embodiments, the mask and/or mask insert is destroyed after removal.

In one aspect, the present disclosure is directed to a mask for testing for a pathogen infection. The mask includes a test substrate including a capture agent for capturing a pathogen.

Suitable capture reagents include, for example, an antibody that specifically binds a pathogen, a ligand that specifically binds the pathogen such as, for example, surface molecules, such as sugars, glycoproteins, and the like, that the pathogen must bind in order to infect its host. Capture reagents can be covalently or noncovalently coupled to the test substrate by a linker. Any suitable linker can be used such as, for example, organic molecules such as a polymer or copolymer (e.g., a substituted or unsubstituted polyalkylene glycol, such as polyethylene glycol), and/or biological molecules such as bovine serum albumin.

In one embodiment, the mask worn by an individual covers the subject's mouth and nose such that pathogen is entrapped and/or adsorbed by the mask material as an individual breathes, coughs and/or sneezes into the mask. The mask can include ear loops, and/or ties to secure the mask to the individual wearer's face. The mask can include strips of material attached to and extending along each side of the mask for use in attaching the mask to the wearer's face and to provide an enhanced fluid seal between the periphery of the mask and the wearer's face.

The test substrate can be coated and/or treated so as to absorb and/or entrap the pathogen.

The mask and/or mask insert portion of mask can be constructed to maximize the surface area of the test substrate. For example, the test substrate can include particles such as microparticles, nanoparticles, and beads, for example. The particles can be coated with the capture agent.

Suitably, the mask and/or the test substrate portion of mask insert can be an immunochromatographic test substrate, a colloidal gold test substrate, and combinations thereof. The substrate can include, for example, quantum dot-marked test substrate, colloidal gold-marked test substrate, colloidal selenium-marked test substrate, upconversion phosphorescence-marked test substrate, nano rare earth fluorescent complex-marked test substrate, temporal resolution chromatography test substrate, chemiluminescence test substrate, and other test substrates.

In embodiments of the mask intended to include a test substrate, the mask is configured to receive the test substrate. The mask can be perforated, for example, and the test substrate can be inserted into the mask at the location of the perforation. In other embodiments, the test substrate can be attached to the mask such as for example, by hook and loop fasteners and sticky adhesives.

The mask insert can also include tabs for marking the mask insert and handling the mask without contaminating the test substrate.

The perforations of the mask insert and particularly the test substrate can be formed such that the test substrate can be separated into different portions (or tabs) as illustrated in FIG. 1. The perforations can be between each tab. Additionally, or alternatively, perforations can be parallel to a top edge (or bottom edge) of the test substrate. As shown in FIGS. 1A and 1B, the perforation can be oriented such that an individual tab can be separated from the label portion in addition to perforations between each tab such that individual tabs can be separated from the test substrate independent of other tabs of the test substrate, leaving the remainder of the tabs attached. Additionally, or alternatively, the test substrate can be perforated along a top edge (or bottom edge) of the test substrate and a space (or gap) can separate each tab such that each tab is independently connected to the top edge or bottom edge of the test substrate as illustrated in FIG. 1B. In another embodiment illustrated in FIG. 1C, tabs can be "free floating" in a test substrate. For example, rather than a single strip with perforations that create 4 tabs, a test substrate can have 4 individual tabs that are unconnected but contained in the same plane of the test substrate. The exemplary embodiments illustrated in FIGS. 1A-1C show 4 tab portions that can be individually tested. For example, the tab 1 can be pooled with other tabs obtained from a plurality of patients. The tab 2 can then be tested individually. The tab 3 can be used as a control. The tab 4 can be stored for future testing. While FIG. 1 illustrates an exemplary embodiment having 4 tabs, it should be understood that the test substrate can have less than 4 tabs and more than 4 tabs. FIG. 2 illustrates a mask on a user with a test substrate having 4 test tabs.

It should be understood that "tabs" can refer to collection substrates alone and to separable portions of the test substrate. For example, a test substrate tab can include one or more protection layers with a collection substrate sandwiched between the protective layers (and other layers). In this embodiment, the test substrate tab (i.e., a portion of the test substrate) can be separated from the remaining test substrate leaving other tab portions undisturbed. In another embodiment, collection substrate tabs can be sandwiched between protective layers. In this embodiment, a collection substrate tab can be independently removed from between the protection layers without the protective layer(s) and/or without touching or disturbing the remaining collection substrate tabs. The advantage of the "teeth" embodiment is that the clinician can simply hold the tab, tear the perforation along the top, which releases both the other and inner layers from the common spine and the inner layer can simply be deposited into a container for further testing. Nothing is contaminated, the outer layer is disposed of, etc. Tabs can also include multiple layers as described herein with respect to multi-layer test substrates. Tab(s) can share a common spine, but be separated (as illustrated in FIG. 1C, for example). Tabs can be perforated for easy removal and non-contamination.

The test substrate can also be a multi-layer test substrate. The multi-layer test substrate has an inner collection substrate that is protected on all sides by additional layers. The inner collection layer is made of a material having high surface area for collecting the pathogen to be detected. The inner collection substrate can also be released from protective layers. The protective layers and inner collection substrate can be made of different materials designed for the specific purposes of the layer (e.g., protection and sample collection). For example, the inner collection substrate can be of a corrugated, double-sided polyester swab material. The inner collection substrate can be coated with a reagent to retain pathogen load collection. The inner collection substrate can also be coated with a reagent to stabilize pathogen material. FIG. 3 depicts a multi-layer test substrate. The protective layer can also function as a transport layer that is a porous and flexible having the capacity to receive and temporarily store exhaled droplet liquid before it is transferred and absorbed by the subjacent collection layer(s). The protective layer can be an air-penetrating, touch-protective coating. The protective layer positioned most distal from the user's face can block all airflow whereas the protective layer positioned most proximal to the user's face can allow airflow.

In some embodiments, the inner collection substrate(s) can separated from the protective layers. In some embodiments, the protective layers can be opened to release or expose inner collection substrates. For example, for an exemplary embodiment having a proximal protective layer and a distal protective layer with an inner collection substrate positioned between the protective layers, the protective layers can be of larger size than the inner collection substrate. When sandwiched together, surfaces of the protective layers can contact each other and be held together using an adhesive, a press-fit locking zipper, tape, or hinge. Separation of the protective layers allows access to the inner collection layer where it can be removed for testing. Separation of protective layers also allows for the insertion or replacement of an unused inner collection substrate.

Features of multi-layer test substrates and multi-layer tabs include, for example, outer layer(s) protect inner layers from contamination, inner layer(s) can be double-sided, inner layer(s) can include adhesives, inner layer(s) can include a stabilizing agent, inner layer(s) can include a testing layer, inner layer(s) can be multi-layered.

In one embodiment, the multi-layer test substrate can include one or more reagent layers (also referred to herein as a "reagent material" that includes an analysis reagent. As used herein, "analysis reagent" refers to components used for detecting the pathogen. For example, analysis reagent can include, for example, buffer components, salts, dNTPs, oligonucleotide primers, polymerases, reverse transcriptases, and combinations thereof. Analysis reagents can suitably be lyophilized, in liquid form, in gels, and combinations thereof. The reagent layer that includes an analysis reagent can be separated by other layers of the test substrate by a coating to prevent the test reagent from contacting the collection layer and/or becoming activated until such time that the test substrate is to be processed for analysis. The analysis reagents can be activated, for example by placing the test substrate (and/or collection layer with dissolvable layer including a test reagent) in a liquid medium such as a buffer including water, whereby the coating dissolves to release the analysis reagent, which can then also dissolve in the buffer. The coating can be meltable, whereby the temperature can be adjusted such that the coating melts to release the analysis reagent and a mixture can form by which a pathogen can be detected. The reagent layer can include microparticles and/or beads that contain analysis reagents.

In some embodiments, the test substrate and inner collection substrate(s) can be packaged in sterilized packaging to prevent contamination during storage and handling. Packaging can be opened to allow the test substrate or inner collection substrate to be then be placed in a mask and/or placed with a protective layer.

The multilayer test substrate can include spacers between individual layers. Spacers may be positioned at the edges of the collection area such that air does not flow through the spacer material. Additionally or alternatively, spacers can be of a material through which air and pathogen particles can pass.

The multilayer test substrate can include a label (see e.g., FIG. 1). The label can be a blank area on which information can be printed. The label can also be pre-printed or have bar code that is machine-readable. The information included on the label can be used to identify the test substrate (including individual test substrate tabs), to track and associate collected test substrates to a user.

In a multilayer test substrate individual layers can have different pore size than other layers. In one exemplary embodiment, the first protective layer can have a pore size having a low filtration efficiency such that pathogen-size particles can freely pass through the protective layer to reach a collection layer.

In an exemplary embodiment, the test substrate can have a first protective layer made of one fiber material with a pore size range that allows pathogen-size particles to freely pass through the first protective layer and at least one collection layer being a different fiber material with a pore size that would be smaller than pathogen-size particles such that pathogen-size particles are captured by the collection layer. Suitably, the collection layer can be a multi-layer laminate itself to increase the viral capture load of each test. If the inner substrate tab can capture a viral density of X, there should be a function of $f(Ln)=Ln \times$ Viral Load of a Single Layer, where Ln is the number of layers. Diminished efficiencies by adding layers need to be understood.

The collection layer(s) can be treated to enhance capture of pathogen particles. In one embodiment, the collection layer is treated with an adhesive to which pathogen particles adhere. In another embodiment, the collection material is treated with a capture ligand. In another exemplary embodiment, the collection material is treated with a combination of adhesive and a capture ligand. Capture ligands can be antibodies, including antibody fragments, aptamers, magnetic particles, and other ligand types that can bind to a pathogen of interest. The capture ligand is intended to attract and retain pathogens such that subsequent analysis can be performed to detect and/or identify the pathogen.

An exemplary multi-layer test substrate includes, for example, a collection layer only without a capture agent and without a protection layer. Another exemplary multi-layer test substrate includes a protective layer and a collection layer. Another exemplary multi-layer test substrate includes a protective layer and a collection layer, wherein the collection substrate includes a capture agent (e.g., an adhesive, a capture ligand, and combinations thereof). Another exemplary multi-layer test substrate includes a protective layer and a plurality of collection layers.

The protective layer can be of a material that allows for airflow and protection of the inner collection layer. Protective layers can be treated or coated with reagents such as anti-microbials, RNAse inhibitors, protease inhibitors, preservatives, and combinations thereof. Protective layers also provide physical protection of the inner collection substrate from touching, for example. Each layer can be perforated to allow separation of tabs.

Orientation of the test substrate can be flat (as in a paper-like sheet), coiled, rod-like, hollow cylindrical-like, honeycomb, and combinations thereof. Coiled substrates, rod-like, and hollow cylindrical shaped substrates can be available axial or perpendicular to breath direction. Coiled substrates, rod-like, and hollow cylindrical shaped substrates can also easily slide into tubes for storage and/or processing. It should be understood that each of these embodiments impart three dimensional structure to enhance collection and permit air flow.

In one aspect, the present disclosure is directed to a method for detecting the presence of a pathogen. In one embodiment, the method detects the presence of a pathogen on an inanimate surface that may come into contact with an individual or a group of individuals. In another embodiment, the method detects the presence of a pathogen infection in a group of individuals wherein at least one individual in the group has or is suspected of having the pathogen infection. The method includes: collecting from the group of individuals a test substrate worn by each individual of the group of individuals; combining the test substrates collected from each individual to form a pooled sample of test substrates; and analyzing the pooled sample of test substrates for the pathogen, wherein detecting the presence of the pathogen in the pooled sample of test substrates indicates that at least one individual in the group of individuals has had close exposure to a pathogen, is infected with the pathogen, or may require further diagnostic testing.

The method can further include independently administering a second test to each individual of the group to identify an individual infected with the pathogen.

In some embodiments, the method is repeated with a sub-group or sub-pool of the first group of individuals. By way of example only, the method of this embodiment includes: collecting from a first group of individuals a test substrate worn by each individual of the group of individuals; combining the test substrates collected from each individual to form a first pooled sample of test substrates; analyzing the first pooled sample of test substrates for the pathogen, wherein detecting the presence of the pathogen in the pooled sample of test substrates indicates that at least one individual in the group of individuals has had close exposure to a pathogen, is infected with the pathogen, or may require further diagnostic testing; collecting from a second group of individuals a test substrate worn by each individual of the group of individuals, wherein the second group of individuals is a sub-group of the first group of individuals; combining the test substrates collected from each individual to form a second pooled sample of test substrates; analyzing the second pooled sample of test substrates for the pathogen, wherein detecting the presence of the pathogen in the pooled sample of test substrates indicates that at least one individual in the group of individuals has had close exposure to a pathogen, is infected with the pathogen, or may require further diagnostic testing. This method can be repeated any number of times to identify the individual or sub-group of individuals or a material substrate in contact with the individual or sub-group of individuals infected with the pathogen.

Suitable test substrates are described herein. Preferably, the test substrate is a mask or a portion of a mask (e.g., mask insert) as described herein.

Suitable pathogens to be tested are described herein.

In one aspect, the present disclosure is directed to a method for detecting the presence of a pathogen infection in an individual having or suspected of having the pathogen infection, the method comprising: collecting from the individual a test substrate worn by the individual; and analyzing the test substrate for the pathogen, wherein detecting the presence of the pathogen indicates that the individual has had close exposure to a pathogen, is infected with the pathogen, or may require further diagnostic testing Suitable test substrates are described herein. Preferably, the test substrate is a mask or a portion of a mask (e.g., mask insert, test substrate, tab) as described herein.

In some embodiments, the pathogen(s) and/or pathogen material to be test for is extracted (eluted or removed) from the test substrate. In some embodiments, the test substrate can be directly analyzed including, for example, embodiments where the test substrate (including tabs, inner test substrate layers, etc.) used is a dissolvable test substrate, a vaporizable test substrate.

Suitable pathogens to be tested are described herein.

The test substrate and the test substrate used in the methods of the present disclosure can be tested directly or removed from the mask such as by cutting the mask to remove a portion of the mask to be tested or the test substrate in the form of a mask insert can be configured so as to be used in an analyzer. Any analyzer used to test a substrate for the presence of an analyte (e.g., a pathogen in the present disclosure) is suitable for use in the present disclosure. In one embodiment, the test substrate can be inserted into an analyzer and the pathogen can be detected by the analyzer. In other embodiments, it should be understood that the analyzer can be a point-of-care analyzer in which the detecting reagents are contacted directly with the test substrate, such as by dropping a solution including detecting reagents directly onto the test substrate. These point-of-care analyzers can be for at home-individual use, use at places of employment and the like. A signal output of the analyzer can provide whether the pathogen is present in the sample. For, example, the signal output by a detector of the analyzer can be transmitted to a data processor for storing, processing and analyzing. Suitably, the test substrate (including tabs) can be placed in an ion-mobility spectrometer and tested for a pathogen.

As illustrated in FIG. 4, the test substrate is compatible with additional sample preparation methods such as mechanical, chemical, and application of forces (e.g., magnetic).

FIG. 5 shows a flow diagram for sample detection using amplification. Following collection, RNA is extracted from the sample and subjected to reverse transcription to create a pool of cDNA. The cDNA is then amplified (using for example, polymerase chain reaction ("PCR") using primers specific for the pathogen of interest. Following amplification, PCR products can be further analyzed. Analysis can include a simple products/no products result and/or PCR products can be sequenced. The amount of product can also be used to determine concentration of pathogen.

Following sample collection via the mask and/or test substrate, the collected sample can be analyzed using commercially available equipment and methods.

Ranges of viral densities and load capacities of the device embodiments above can be determined by exploiting a ratio based on internal, controlled spike tests on masks.

An approximate range of viral load collected by embodiments of the test substrate device can be inferred with infected humans wearing the device under different conditions using the assumption: $VD_{d1}/VD_{m1}:VD_{d2}/VD_{m2}$, where VD=a normalized Viral Density of inner substrate based on viral load per square millimeter ($mm^2$); d1=pathogen-spiked device in a mask; m1=pathogen-spiked mask with device in mask; d2=inferred performance of device embodiments; m2=masks collected from shedding patients. Once the range of results of the pathogen-spiked test and from the collected masks is determined, an approximate range of the device embodiment's collection potential can be inferred. In another example, test substrate devices can be spiked with a range of viral loads to simulate a low, average, and high density to infer viral loads that can be collected with test substrate devices in use. Projected device sensitivity can be determined based on a range of pool sizes and a range of densities.

Viral load and number of layers of test substrate can be determined using the equation: $f(Ln)=VD$ of Single Layer$\times$ Ln. Without being bound by theory, there may be diminishing returns with more layers that need to be built into the function since expelled air may not be able to get to inner layers as efficiently. Some devices may only require 1-5 layers to screen smaller pools while other devices with greater numbers of layers can be useful to screen larger pools.

The range of viral load collection capability of test substrates can also be determined as a function of time worn. Embodiments of devices can be tested at two or more time points. Viral load can be quantified based on the amount of time each embodiment is worn.

EXAMPLES

In this Example, detection of COVID-19 using swabs to collect samples was compared to detection using a mask insert. Patients who were presumed positive with COVID-19 wore a mask containing a mask insert for 30-60 minutes. After the device was removed from the mask, the test substrate was removed and analyzed by RT-PCR. Concurrently, patients were swabbed with a nasal swab and the swab was also tested with RT-PCR. The Nasal swab and mask insert results were compared as summarized in Table 1.

TABLE 1

| Clinical Results of RT-PCR Testing. | | | |
|---|---|---|---|
| Patient # (Day) | Detected on Swab | Detected on Mask Insert | Test Notes |
| 101(1) | Yes | Yes | TaqPath Molecular Test |
| 101(3) | Yes | Yes | TaqPath Molecular Test |
| 102(1) | Yes | No | Weak swab PCR positive with ct > 35 |
| 103(1) | Yes | Yes | TaqPath Molecular Test |
| 102(3) | Yes | Yes | TaqPath Molecular Test |
| | No | No | Patient Negative |
| 105(1) | Yes | Yes | TaqPath Molecular Test |
| 106(1) | No | No | Patient Negative |
| 107(1) | Yes | Yes | TaqPath Molecular Test |
| 108(1) | Yes | Yes | TaqPath Molecular Test |
| 110(1) | Yes | No | TaqPath Molecular Test |
| 111(1) | Yes | Yes | TaqPath Molecular Test |
| 111(1) | Yes | Yes | TaqCheck Test |
| 201(1) | Yes | No | In ambient temperature for > 96 hours |
| 201(1) | Yes | Yes | TaqCheck Test |
| 112(1) | Yes | No | Weak swab PCR positive withct > 35 |

The compositions, devices and methods of the present disclosure allow for the rapid and large-scale identification of a pathogen infection in a group of individuals or an inanimate surface that has come into contact with an individual and/or group of individuals in a single test. If a positive test result is obtained in the pooled sample, individuals or sub-groups of individuals of the pooled sample can be separately re-tested to identify the individual and/or individuals who are infected. The method may also identify individuals who are exposed through contact with the positively identified infected individual(s). Subsequent steps can then be taken to isolate both positively infected individuals and those who are exposed to the positively infected individuals to possibly prevent spread of the infection. The compositions, devices and methods of the present disclosure also reduce the cost associated with individually testing of a population because 1) a single test can be administered to a group of individuals and 2) a relatively inexpensive insert can be used such to allow for reuse of the mask. Administering a single test to an individual, group of individuals and/or sub-group of individuals reduces the time it takes to conduct a test on multiple individuals separately. The methods of the present disclosure also reduces the amounts of reagents needed to conduct a single test as compared to the amount of reagents required to separately test multiple individuals. Further, the methods of the present disclosure allow for limited invasive testing, such to eliminate the discomfort associated with conventional serological or nasal testing methods.

What is claimed is:

1. A mask insert comprising a first layer, a test substrate for capturing an analyte in an air sample obtained from a subject, and a second layer, wherein the first layer and the second layer form an outer layer surrounding the test substrate, the first and second layer comprising a nonwoven web, wherein overlapping regions of the first layer and the second layer are bonded, forming a bonded area and reducing air flow through the mask insert in the bonded area and directing air flow toward the test substrate, wherein at least a portion of the test substrate is bonded to at least one of the first layer and the second layer, wherein the test substrate is configured to be separated from at least a portion of the outer layer, and wherein the mask insert is configured for coupling to a surface of a face mask.

2. The mask insert of claim 1, further comprising a fastener on a surface of at least one of the first layer or the second layer and configured to couple the mask insert to a surface of a face mask.

3. The mask insert of claim 1, further comprising a perforation in the outer layer proximate to an end of the mask insert.

4. The mask insert of claim 3, further comprising a notch coextensive with the perforation.

5. The mask insert of claim 1, wherein the test substrate comprises a material selected from the group consisting of synthetic fibers, natural fibers, and combinations thereof.

6. The mask insert of claim 5, wherein the test substrate comprises a material selected from the group consisting of hydrophobic fibers, hydrophilic fibers, and combinations thereof.

7. The mask insert of claim 6, wherein the hydrophobic fibers are selected from the group consisting of polypropylene, polylactone, poly(caprolactone), poly (L-lactic acid), poly (glycolic acid), co-poly(alkyl acrylate), polybutadiene, polyethylene, polystyrene, polyacrylonitrile, polyethylene (terephthalate), polysulfone, polycarbonate, poly(vinyl chloride), and combinations thereof.

8. The mask insert of claim 6, wherein the hydrophilic fibers are selected from the group consisting of linear poly(ethylenimine), cellulose, cellulose acetate and other grafted cellulosics, poly (hydroxyethylmethacrylate), poly (ethyleneoxide), polyvinylpyrrolidone, poly(acrylic acid), poly(ethylene glycol), poly(vinyl alcohol), poly (vinyl acetate), poly(acrylamide), proteins, poly (vinyl pyrrolidone), poly(styrene sulfonate), and combinations thereof.

9. The mask insert of claim 5, wherein the test substrate comprises a material selected from the group consisting of acrylonitrile/butadiene copolymer, cellulose, cellulose acetate, chitosan, collagen, DNA, fibrinogen, fibronectin, nylon, poly(acrylic acid), poly(chloro styrene), poly(dimethyl siloxane), poly(ether imide), poly(ether sulfone), poly (ethyl acrylate), poly(ethyl vinyl acetate), poly(ethyl-co-vinyl acetate), poly(ethylene oxide), poly(ethylene terephthalate), poly(lactic acid-co-glycolic acid), poly (methacrylic acid) salt, poly(methyl methacrylate), poly (methyl styrene), poly(styrene sulfonic acid) salt, poly(styrene sulfonyl fluoride), poly(styrene-co-acrylonitrile), poly (styrene-co-butadiene), poly(styrene-co-divinyl benzene), poly(vinyl acetate), poly(vinyl alcohol), poly(vinyl chloride), poly(vinylidene fluoride), polyacrylamide, polyacrylonitrile, polyamic acid (PAA), polyamide, polyaniline, polybenzimidazole, polycaprolactone, polycarbonate, polydimethylsiloxane-co-polyethyleneoxide, polyetheretherketone, polyethylene, polyethyleneimine, polyimide, polyisoprene, polylactide, polypropylene, polystyrene, polysulfone, polyurethane, polyvinylpyrrolidone, proteins, SEBS copolymer, silk, styrene/isoprene copolymer, poly (vinylidene fluoride)-blend-poly(methyl methacrylate), polystyrene-blend-poly(vinylmethylether), poly(methyl methacrylate)-blend-poly(ethyleneoxide), poly(hydroxypropyl methacrylate)-blend poly(vinylpyrrolidone), poly(hydroxybutyrate)-blend-poly(ethylene oxide), protein blend-polyethyleneoxide, polylactide-blend-polyvinylpyrrolidone, polystyrene-blend-polyester, polyester-blend-poly(hydroxyethyl methacrylate), poly(ethylene oxide)-blend poly (methyl methacrylate), poly(hydroxystyrene)-blend-poly (ethylene oxide), and combinations thereof.

10. The mask insert of claim 1, wherein the test substrate comprises electret.

11. The mask insert of claim 1, wherein the first layer and the second layer comprise synthetic fibers, natural fibers, and combinations thereof.

12. The mask insert of claim 1, further comprising an assay selected from the group consisting of a vertical flow assay and a lateral flow assay.

13. The mask insert of claim 1, further comprising a buffer dispensing device.

14. A system for detecting an analyte in an air sample obtained from a subject, the system comprising:

a mask insert, the mask insert comprising: a first layer, a test substrate for capturing an analyte in an air sample obtained from a subject, a second layer, the first and second layer comprising a nonwoven web, wherein the first layer and the second layer form an outer layer surrounding the test substrate, wherein overlapping regions of the first layer and the second layer are bonded, forming a bonded area and reducing air flow through the mask insert in the bonded area and directing air flow toward the test substrate, wherein at least a portion of the test substrate is bonded to at least one of the first layer and the second layer, and wherein the test substrate is configured to be separated from at least a portion of the outer layer; and a mask worn by the subject, wherein the mask insert is coupled to a surface of the mask.

15. The system of claim 14, wherein the mask insert is coupled with one of a vertical flow assay and a lateral flow assay.

16. The system of claim 14, wherein the mask insert further comprises a buffer dispensing device.

17. The system of claim 14, wherein the test substrate comprises synthetic fibers, natural fibers, and combinations thereof.

18. The system of claim 15, wherein the test substrate comprises electret.

19. The system of claim 14, wherein the first layer and the second layer comprise synthetic fibers, natural fibers, and combinations thereof.

* * * * *